(12) United States Patent
Sakamoto et al.

(10) Patent No.: US 10,729,640 B2
(45) Date of Patent: Aug. 4, 2020

(54) AQUEOUS GELLING AGENT COMPOSITION AND COSMETICS USING SAME

(71) Applicant: ADEKA CORPORATION, Tokyo (JP)

(72) Inventors: Takao Sakamoto, Tokyo (JP); Yasuhiro Tsushima, Tokyo (JP); Yuki Takeishi, Tokyo (JP)

(73) Assignee: ADEKA CORPORATION, Tokyo (JP)

( * ) Notice: Subject to any disclaimer, the term of this patent is extended or adjusted under 35 U.S.C. 154(b) by 0 days.

(21) Appl. No.: 16/327,557

(22) PCT Filed: Aug. 28, 2017

(86) PCT No.: PCT/JP2017/030671
§ 371 (c)(1),
(2) Date: Feb. 22, 2019

(87) PCT Pub. No.: WO2018/043374
PCT Pub. Date: Mar. 8, 2018

(65) Prior Publication Data
US 2019/0328649 A1 Oct. 31, 2019

(30) Foreign Application Priority Data
Aug. 31, 2016 (JP) ................. 2016-168932

(51) Int. Cl.
*A61K 8/87* (2006.01)
*A61K 8/04* (2006.01)
*A61K 8/34* (2006.01)

(52) U.S. Cl.
CPC ............... *A61K 8/87* (2013.01); *A61K 8/042* (2013.01); *A61K 8/046* (2013.01); *A61K 8/345* (2013.01); *A61K 2800/87* (2013.01)

(58) Field of Classification Search
CPC ........ A61K 8/345; A61K 8/042; A61K 8/046; A61K 8/87; A61K 2800/87; C09K 3/00; A61Q 19/00
See application file for complete search history.

(56) References Cited

U.S. PATENT DOCUMENTS

| | | | | |
|---|---|---|---|---|
| 2004/0105836 A1* | 6/2004 | Seipel | ............ | A61K 8/87 424/70.17 |
| 2005/0187342 A1* | 8/2005 | Schieferstein | ..... | C08G 18/2825 524/591 |
| 2009/0209659 A1* | 8/2009 | Di Cosmo | .......... | A61K 8/37 514/772.3 |
| 2016/0120779 A1* | 5/2016 | Sakamoto | .......... | A61K 8/042 514/788 |

* cited by examiner

*Primary Examiner* — Blessing M Fubara
(74) *Attorney, Agent, or Firm* — Wenderoth, Lind & Ponack, L.L.P.

(57) ABSTRACT

Provided is an aqueous gelling agent composition, including: compound (A) represented by the general formula (1); and compound (B) represented by the general formula (2), wherein a mass ratio of compound (A) to compound (B), (A): (B), is from 95:5 to 85:15:

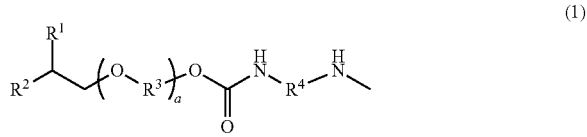

(1)

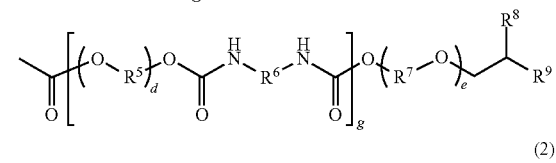

(2)

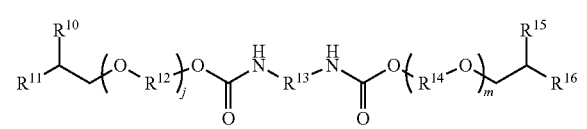

where $R^1$, $R^2$, $R^8$, $R^9$, $R^{10}$, $R^{11}$, $R^{15}$, and $R^{16}$ each independently represent a hydrocarbon group having 4 to 20 carbon atoms, $R^3$, $R^5$, $R^7$, $R^{12}$, and $R^{14}$ each independently represent a divalent hydrocarbon group having 2 to 4 carbon atoms, $R^4$, $R^6$, and $R^{13}$ each independently represent a divalent hydrocarbon group having 3 to 16 carbon atoms, a, e, j, and m each independently represent a number of 10 to 100, d represents a number of 100 to 500, and g represents a number of 1 to 10.

5 Claims, No Drawings

AQUEOUS GELLING AGENT COMPOSITION AND COSMETICS USING SAME

TECHNICAL FIELD

The present invention relates to an aqueous gelling agent composition that gives an elastic and soft gel having a self-leveling property and being usable with a spray bottle.

BACKGROUND ART

An aqueous viscosity modifier (sometimes referred to as "thickener" or "gelling agent") is generally used in various fields, such as paints, adhesives and pressure-sensitive adhesives, foods, and cosmetics. By being added to various products, the aqueous viscosity modifier can increase viscosities of the products to impart various functions thereto. For example, an oil-in-water emulsified composition to be used for, for example, a drug, a quasi-drug, or a milky lotion serving as a cosmetic is generally changed in viscosity (e.g., thickening or gelation) using a viscosity modifier. This is because the change in viscosity results in various effects, such as an improvement in spread on a skin and achievement of a unique feeling. A degree to which the viscosity is changed greatly varies for each product. For example, the product is greatly thickened like a cream in some cases, or the viscosity is changed without a significant change in apparent viscosity like a face lotion in other cases.

In recent years, in the field of cosmetics, an "all-in-one cosmetic" has been attracting attention as a basic cosmetic. In general, as kinds of the basic cosmetic, there are given a face lotion, a milky lotion, a beauty serum, a cream, and the like, each of which plays a different role. Examples thereof include the following: the face lotion "delivers a moisturizing component to the stratum corneum"; the beauty serum "keeps moisture supplied by the face lotion and gives the skin a special nutrient to further enhance the moisturizing effect"; and the milky lotion or the cream "holds the moisture of the skin to recover the barrier function of the skin." The "all-in-one cosmetic" is a very highly functional and convenient cosmetic that allows those roles to be covered by one cosmetic. The "all-in-one cosmetic" is in very high demand, and is also required by the market to have high performance.

The performance required of the gelling agent to be used for the "all-in-one cosmetic" is as follows: the gelling agent gives a characteristic gel needed for giving a satisfactory feeling of use, supplying moisture to the skin, and keeping moisture for a long period of time. Features of this gel include, for example, having elasticity for keeping a gel state when the gel is taken in a hand, and having softness for ease of spread on the skin. Further, a gel that is also less restricted in terms of its container is preferred, and for example, there is a demand for a gel that can be used even with a wide-mouth container with a lid or a spray bottle, without any problem. Particularly when contained in the wide-mouth container with a lid, a gel having such a self-leveling property that, when the gel is taken out with fingers to be taken in a hand, the remaining gel in the container spontaneously returns to a leveled state provides a fresh feeling and a sanitary feeling when next used, and hence tends to be highly evaluated by users. In addition, when contained in the spray bottle, a characteristic gel that is jetted like water through application of a shearing stress thereto by a spraying operation, and returns to a gel-like state on the skin is more highly evaluated by users as a functional and convenient cosmetic.

As gelling agents usable for cosmetics, for example, there are generally known: a natural gelling agent, such as carboxymethylcellulose or hydroxyethylcellulose; an alkali thickening type gelling agent of a type that thickens with an alkali, such as polyacrylic acid or a polyacrylic acid-containing copolymer; and a urethane-type gelling agent, such as urethane-modified polyether. Of those, as compared to other gelling agents, the urethane-type gelling agent has been produced in many kinds and frequently used for, for example, the following reasons: various kinds thereof can be freely produced; the urethane-type gelling agent can impart a variety of viscosities to products by being added thereto; and the urethane-type gelling agent is hardly affected by a pH or a salt (for example, Patent Documents 1 to 7).

Patent Document 1: JP 2014-523933 A

Patent Document 2: JP 2008-505232 A

Patent Document 3: JP 2007-217700 A

Patent Document 4: JP 2004-525995 A

Patent Document 5: JP 2000-239649 A

Patent Document 6: JP H11-199854 A

Patent Document 7: WO 2014/084174

SUMMARY OF INVENTION

Technical Problem

The urethane-type gelling agents described in Patent Documents 5 and 6 among the above-mentioned patent documents each give an "elastic and soft gel" that is easy to use as a gel for an "all-in-one cosmetic". However, although giving an "elastic and soft gel," those additives may be said to be insufficient in terms of performance regarding a self-leveling property and a feeling of use when used with a spray bottle. In the market, there is a demand for the development of a gelling agent that gives an elastic and soft gel having a sufficient self-leveling property and being usable with a spray bottle.

Therefore, a problem to be solved by the present invention is to provide an aqueous gelling agent composition that gives an elastic and soft gel having a satisfactory self-leveling property and being usable with a spray bottle.

Solution to the Problem

In view of the foregoing, the inventors of the present invention have made extensive investigations and found an aqueous gelling agent composition that gives an elastic and soft gel having a satisfactory self-leveling property and being usable with a spray bottle. Thus, the inventors have completed the present invention. That is, according to one embodiment of the present invention, there is provided an aqueous gelling agent composition, including: compound (A) represented by the following general formula (1); and compound (B) represented by the following general formula (2), wherein a mass ratio of compound (A) to compound (B), (A):(B), is from 95:5 to 85:15:

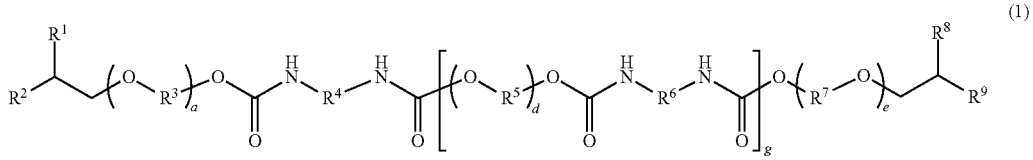

where $R^1$, $R^2$, $R^8$, and $R^9$ each independently represent a hydrocarbon group having 4 to 20 carbon atoms, $R^3$, $R^5$, and $R^7$ each independently represent a divalent hydrocarbon group having 2 to 4 carbon atoms, $R^4$ and $R^6$ each independently represent a divalent hydrocarbon group having 3 to 16 carbon atoms, a and e each independently represent a number of 10 to 100, d represents a number of 100 to 500, and g represents a number of 1 to 10; and

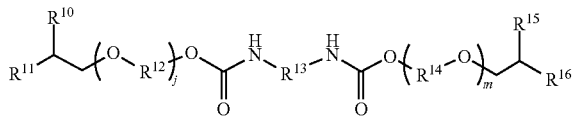

where $R^{10}$, $R^{11}$, $R^{15}$, and $R^{16}$ each independently represent a hydrocarbon group having 4 to 20 carbon atoms, $R^{12}$ and $R^{14}$ each independently represent a divalent hydrocarbon group having 2 to 4 carbon atoms, $R^{13}$ represents a divalent hydrocarbon group having 3 to 16 carbon atoms, and j and m each independently represent a number of 10 to 100.

Advantageous Effects of the Invention

The effect of the present invention lies in providing the aqueous gelling agent composition that gives an elastic and soft gel having a satisfactory self-leveling property and being usable with a spray bottle.

DESCRIPTION OF EMBODIMENTS

First, terms used herein are defined. As used herein, the term "self-leveling property" refers to a property of spontaneously returning to an original level surface when a physical stimulus is applied to a gel (e.g., the gel is scooped up or the gel is stirred). In addition, the term "usable with a spray bottle" refers to a property of exhibiting the behavior of an elastic and soft gel when contained in the spray bottle and being easily sprayed like water when sprayed from the spray bottle (when a shearing stress is applied to the gel).

An aqueous gelling agent composition of the present invention is an aqueous gelling agent composition that gives an elastic and soft gel having both the above-mentioned two performances, i.e., having a "self-leveling property" and being "usable with a spray bottle." Through the use of the aqueous gelling agent composition of the present invention, a gel-like aqueous cosmetic having a self-leveling property and being usable with a spray bottle can be obtained.

Compound (A) to be used in the present invention is a compound represented by the following general formula (1):

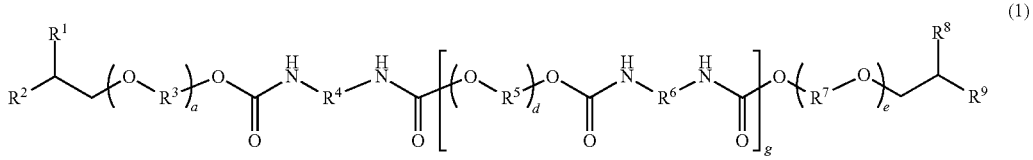

where $R^1$, $R^2$, $R^8$, and $R^9$ each independently represent a hydrocarbon group having 4 to 20 carbon atoms, $R^3$, $R^5$, and $R^7$ each independently represent a divalent hydrocarbon group having 2 to 4 carbon atoms, $R^4$ and $R^6$ each independently represent a divalent hydrocarbon group having 3 to 16 carbon atoms, and a and e each independently represent a number of 10 to 100, d represents a number of 100 to 500, and g represents a number of 1 to 10.

In the general formula (1), $R^1$, $R^2$, $R^8$, and $R^9$ each independently represent a hydrocarbon group having 4 to 20 carbon atoms. Examples of such group include: a saturated aliphatic hydrocarbon group, such as a n-butyl group, an isobutyl group, a s-butyl group, a t-butyl group, a n-pentyl group, a branched pentyl group, a secondary pentyl group, a tertiary pentyl group, a n-hexyl group, a branched hexyl group, a secondary hexyl group, a tertiary hexyl group, a n-heptyl group, a branched heptyl group, a secondary heptyl group, a tertiary heptyl group, a n-octyl group, a 2-ethylhexyl group, a branched octyl group, a secondary octyl group, a tertiary octyl group, a n-nonyl group, a branched nonyl group, a secondary nonyl group, a tertiary nonyl group, a n-decyl group, a branched decyl group, a secondary decyl group, a tertiary decyl group, a n-undecyl group, a branched undecyl group, a secondary undecyl group, a tertiary undecyl group, a n-dodecyl group, a branched dodecyl group, a secondary dodecyl group, a tertiary dodecyl group, a n-tridecyl group, a branched tridecyl group, a secondary tridecyl group, a tertiary tridecyl group, a n-tetradecyl group, a branched tetradecyl group, a secondary tetradecyl group, a tertiary tetradecyl group, a n-pentadecyl group, a branched pentadecyl group, a secondary pentadecyl group, a tertiary pentadecyl group, a n-hexadecyl group, a branched hexadecyl group, a secondary hexadecyl group, a tertiary hexadecyl group, a n-heptadecyl group, a branched heptadecyl group, a secondary heptadecyl group, a tertiary heptadecyl group, a n-octadecyl group, a branched octadecyl group, a secondary octadecyl group, a tertiary octadecyl group, a n-nonadecyl group, a branched nonadecyl group, a secondary nonadecyl group, a tertiary nonadecyl group, a n-icosyl group, a branched icosyl group, a secondary icosyl group, or a tertiary icosyl group; an unsaturated aliphatic hydrocarbon group, such as a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, a 5-hexenyl group, a 1-heptenyl group, a 6-heptenyl group, a 1-octenyl group, a 7-octenyl group, a 8-nonenyl group, a 1-decenyl group, a 9-decenyl group, a 10-undecenyl group, a 1-dodecenyl group, a 4-dodecenyl group, a 11-dodecenyl group, a 12-tridecenyl group, a 13-tetradecenyl group, a 14-pentadecenyl group, a 15-hexadecenyl group, a 16-heptadecenyl group, a 1-octadecenyl group, a 17-octadecenyl group, a 1-nonadecenyl group, or a 1-icosenyl group; an aromatic hydrocarbon group, such as a phenyl group, a toluyl group, a xylyl group, a cumenyl group, a mesityl group, a benzyl group, a phenethyl group, a styryl group, a cinnamyl group, a benzhydryl group, a trityl group, an ethylphenyl group, a propylphenyl group, a butylphenyl group, a pentylphenyl group, a hexylphenyl group, a heptylphenyl group, an octylphenyl group, a nonylphenyl group, a decylphenyl group, an undecylphenyl group, a dodecylphenyl group, a styrenated phenyl group, a p-cumylphenyl group, a phenylphenyl group, a benzylphenyl group, an α-naphthyl group, or a R-naphthyl group; and an alicyclic hydrocarbon group, such as a cyclopropyl group, a cyclobutyl group, a cyclopentyl group, a cyclohexyl group, a cycloheptyl group, a cyclooctyl group, a methylcyclopentyl group, a methylcyclohexyl group, a methylcycloheptyl group, a methylcyclooctyl group, a 4,4,6,6-tetramethylcyclohexyl group, a 1,3-dibutylcyclohexyl group, a norbornyl group, a bicyclo[2.2.2]octyl group, an adamantyl group, a 1-cyclobutenyl group, a 1-cyclopentenyl group, a 3-cyclopentenyl group, a 1-cyclohexenyl group, a 3-cyclohexenyl group, a 3-cycloheptenyl group, a 4-cyclooctenyl group, a 2-methyl-3-cyclohexenyl group, or a 3,4-dimethyl-3-cyclohexenyl group. $R^1$, $R^2$, $R^8$, and $R^9$ may be identical to each other, or may be different from each other. Of those, from the viewpoints of obtaining a compound with which the effect of the present invention is easily obtained, and easily achieving raw material procurement and production, $R^1$, $R^2$, $R^8$, and $R^9$ each represent preferably a saturated aliphatic hydrocarbon group or an unsaturated aliphatic hydrocarbon group, more preferably a saturated aliphatic hydrocarbon group, still more preferably a saturated aliphatic hydrocarbon group having 5 to 18 carbon atoms, even more preferably a saturated aliphatic hydrocarbon group having 8 to 15 carbon atoms, most preferably a saturated aliphatic hydrocarbon group having 10 to 12 carbon atoms.

In the general formula (1), $R^3$, $R^5$, and $R^7$ each independently represent a divalent hydrocarbon group having 2 to 4 carbon atoms. Examples of such group include: an ethylene group; a propane-1,3-diyl (linear propylene) group; a branched propylene group, such as a propane-1,2-diyl group or a propane-2,2-diyl group; a linear butylene group, such as a butane-1,4-diyl group, a butane-1,2-diyl group, a butane-1,3-diyl group, a butane-2,3-diyl group, a butane-1,1-diyl group, or a butane-2,2-diyl group; and a branched butylene group, such as a 2-methylpropane-1,3-diyl group or a 2-methylpropane-1,2-diyl group. Of those, from the viewpoint of obtaining a compound with which the effect of the present invention is easily obtained, $R^3$, $R^5$, and $R^7$ each represent preferably a divalent linear hydrocarbon group having 2 to 4 carbon atoms, more preferably an ethylene group or a propane-1,3-diyl (linear propylene) group, still more preferably an ethylene group. $R^3$s may all represent identical groups, or may represent different groups, $R^5$s also may all represent identical groups, or may represent different groups, and $R^7$s also may all represent identical groups, or may represent different groups.

In the general formula (1), $R^4$ and $R^6$ each independently represent a divalent hydrocarbon group having 3 to 16 carbon atoms. An example of such group is a divalent aliphatic hydrocarbon group, aromatic hydrocarbon group, or alicyclic hydrocarbon group having 3 to 16 carbon atoms. Any of those hydrocarbon groups may be adopted as long as the number of carbon atoms falls within the range of from 3 to 16, but a group obtained by removing two isocyanate groups from a diisocyanate compound represented by the general formula (5) described later is preferred. This group is described in detail in the description of the diisocyanate compound to be described later.

In the general formula (1), a and e each independently represent a number of 10 to 100. Of those, from the viewpoint of easily producing or obtaining a raw material, the number is preferably from 12 to 50, more preferably from 15 to 30.

In the general formula (1), d represents a number of 100 to 500. Of those, from the viewpoint of obtaining a compound with which the effect of the present invention is easily obtained, the number is preferably from 120 to 450, more preferably from 150 to 400, still more preferably from 180 to 350, most preferably from 200 to 300.

In the general formula (1), g represents a number of 1 to 10. Of those, from the viewpoint of obtaining a compound with which the effect of the present invention is easily obtained, the number is preferably from 1 to 8, more preferably from 1 to 6, and a mixture of compounds in each of which g represents from 1 to 6 is still more preferred.

Compound (B) to be used in the present invention is a compound represented by the following general formula (2). Compound (B) functions like a gelation promoter, and thus exhibits a synergistic effect with compound (A) represented by the general formula (1) to give a characteristic gel that is the effect of the present invention. Therefore, without compound (B), the effect of the present invention is not obtained.

(2)

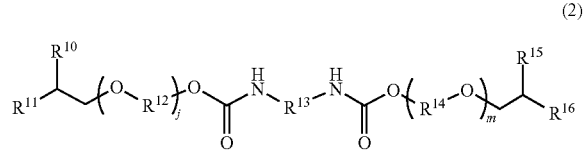

In the formula, $R^{10}$, $R^{11}$, $R^{15}$, and $R^{16}$ each independently represent a hydrocarbon group having 4 to 20 carbon atoms, $R^{12}$ and $R^{14}$ each independently represent a divalent hydrocarbon group having 2 to 4 carbon atoms, $R^{13}$ represents a divalent hydrocarbon group having 3 to 16 carbon atoms, and j and m each independently represent a number of 10 to 100.

In the general formula (2), $R^{10}$, $R^{11}$, $R^{15}$, and $R^{16}$ each independently represent a hydrocarbon group having 4 to 20 carbon atoms. Examples of such group include: a saturated aliphatic hydrocarbon group, such as a n-butyl group, an isobutyl group, a s-butyl group, a t-butyl group, a n-pentyl group, a branched pentyl group, a secondary pentyl group, a tertiary pentyl group, a n-hexyl group, a branched hexyl group, a secondary hexyl group, a tertiary hexyl group, a n-heptyl group, a branched heptyl group, a secondary heptyl group, a tertiary heptyl group, a n-octyl group, a 2-ethylhexyl group, a branched octyl group, a secondary octyl group, a tertiary octyl group, a n-nonyl group, a branched nonyl group, a secondary nonyl group, a tertiary nonyl group, a n-decyl group, a branched decyl group, a secondary decyl group, a tertiary decyl group, a n-undecyl group, a branched undecyl group, a secondary undecyl group, a tertiary undecyl group, a n-dodecyl group, a branched dodecyl group, a secondary dodecyl group, a tertiary dodecyl group, a n-tridecyl group, a branched tridecyl group, a secondary tridecyl group, a tertiary tridecyl group, a n-tetradecyl group, a branched tetradecyl group, a secondary tetradecyl group, a tertiary tetradecyl group, a n-pentadecyl group, a branched pentadecyl group, a secondary pentadecyl group, a tertiary pentadecyl group, a n-hexadecyl group, a branched hexadecyl group, a secondary hexadecyl group, a tertiary hexadecyl group, a n-heptadecyl group, a branched heptadecyl group, a secondary heptadecyl group, a tertiary heptadecyl group, a n-octadecyl group, a branched octadecyl group, a secondary octadecyl group, a tertiary octadecyl group, a n-nonadecyl group, a branched nonadecyl group, a secondary nonadecyl group, a tertiary nonadecyl group, a n-icosyl group, a branched icosyl group, a secondary icosyl group, or a tertiary icosyl group; an unsaturated aliphatic hydrocarbon group, such as a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, a 5-hexenyl group, a 1-heptenyl group, a 6-heptenyl group, a 1-octenyl group, a 7-octenyl group, a 8-nonenyl group, a 1-decenyl group, a 9-decenyl group, a 10-undecenyl group, a 1-dodecenyl group, a 4-dodecenyl group, a 11-dodecenyl group, a 12-tridecenyl group, a 13-tetradecenyl group, a 14-pentadecenyl group, a 15-hexadecenyl group, a 16-heptadecenyl group, a 1-octadecenyl group, a 17-octadecenyl group, a 1-nonadecenyl group, or a 1-icosenyl group; an aromatic hydrocarbon group, such as a phenyl group, a toluyl group, a xylyl group, a cumenyl group, a mesityl group, a benzyl group, a phenethyl group, a styryl group, a cinnamyl group, a benzhydryl group, a trityl group, an ethylphenyl group, a propylphenyl group, a butylphenyl group, a pentylphenyl group, a hexylphenyl group, a heptylphenyl group, an octylphenyl group, a nonylphenyl group, a decylphenyl group, an undecylphenyl group, a dodecylphenyl group, a styrenated phenyl group, a p-cumylphenyl group, a phenylphenyl group, a benzylphenyl group, an α-naphthyl group, or a β-naphthyl group; and an alicyclic hydrocarbon group, such as a cyclopropyl group, a cyclobutyl group, a cyclopentyl group, a cyclohexyl group, a cycloheptyl group, a cyclooctyl group, a methylcyclopentyl group, a methylcyclohexyl group, a methylcycloheptyl group, a methylcyclooctyl group, a 4,4,6,6-tetramethylcyclohexyl group, a 1,3-dibutylcyclohexyl group, a norbornyl group, a bicyclo[2.2.2]octyl group, an adamantyl group, a 1-cyclobutenyl group, a 1-cyclopentenyl group, a 3-cyclopentenyl group, a 1-cyclohexenyl group, a 3-cyclohexenyl group, a 3-cycloheptenyl group, a 4-cyclooctenyl group, a 2-methyl-3-cyclohexenyl group, or a 3,4-dimethyl-3-cyclohexenyl group. $R^{10}$, $R^{11}$, $R^{15}$, and $R^{16}$ may be identical to each other, or may be different from each other. Of those, from the viewpoints of obtaining a compound with which the effect of the present invention is easily obtained, and easily achieving raw material procurement and production, $R^{10}$, $R^{11}$, $R^{15}$, and $R^{16}$ each represent preferably a saturated aliphatic hydrocarbon group or an unsaturated aliphatic hydrocarbon group, more preferably a saturated aliphatic hydrocarbon group, still more preferably a saturated aliphatic hydrocarbon group having 5 to 18 carbon atoms, even more preferably a saturated aliphatic hydrocarbon group having 8 to 15 carbon atoms, most preferably a saturated aliphatic hydrocarbon group having 10 to 12 carbon atoms.

In the general formula (2), $R^{12}$ and $R^{14}$ each independently represent a divalent hydrocarbon group having 2 to 4 carbon atoms. Examples of such group include: an ethylene group; a propane-1,3-diyl (linear propylene) group; a branched propylene group, such as a propane-1,2-diyl group or a propane-2,2-diyl group; a linear butylene group, such as a butane-1,4-diyl group, a butane-1,2-diyl group, a butane-1,3-diyl group, a butane-2,3-diyl group, a butane-1,1-diyl group, or a butane-2,2-diyl group; and a branched butylene group, such as a 2-methylpropane-1,3-diyl group or a 2-methylpropane-1,2-diyl group. Of those, from the viewpoint of obtaining a compound with which the effect of the present invention is easily obtained, $R^{12}$ and $R^{14}$ each represent preferably a divalent linear hydrocarbon group having 2 to 4 carbon atoms, more preferably an ethylene group or a propane-1,3-diyl (linear propylene) group, still more preferably an ethylene group. $R^{12}$s may all represent identical groups, or may represent different groups, and $R^{14}$s also may all represent identical groups, or may represent different groups.

In the general formula (2), $R^{13}$ represents a divalent hydrocarbon group having 3 to 16 carbon atoms. An example of such group is a divalent aliphatic hydrocarbon group, aromatic hydrocarbon group, or alicyclic hydrocarbon group having 3 to 16 carbon atoms. Any of those hydrocarbon groups may be adopted as long as the number of carbon atoms falls within the range of from 3 to 16, but a group obtained by removing two isocyanate groups from a diisocyanate compound represented by the general formula (7) described later is preferred. This group is described in detail in the description of the diisocyanate compound to be described later.

In the general formula (2), j and m each independently represent a number of 10 to 100. Of those, from the viewpoint of easily producing or obtaining a raw material, the number is preferably from 12 to 50, more preferably from 15 to 30.

A production method for the compound represented by the general formula (1) is not particularly limited, and the compound may be produced using any known production method without any problem, but is preferably synthesized using compounds represented by the following general formulae (3) to (5) as raw materials because such method is simple and inexpensive.

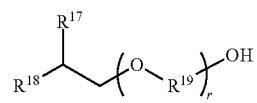

(3)

In the formula, $R^{17}$ and $R^{18}$ each independently represent a hydrocarbon group having 4 to 20 carbon atoms, $R^{19}$ represents a divalent hydrocarbon group having 2 to 4 carbon atoms, and r represents a number of 10 to 100.

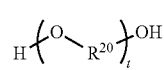

(4)

In the formula, $R^{20}$ represents a divalent hydrocarbon group having 2 to 4 carbon atoms, and t represents a number of 100 to 500.

$$OCN-Q-NCO \quad (5)$$

In the formula, Q represents a divalent hydrocarbon group having 3 to 16 carbon atoms.

In the general formula (3), $R^{17}$ and $R^{18}$ each independently represent a hydrocarbon group having 4 to 20 carbon atoms. Examples of such group include: a saturated aliphatic hydrocarbon group, such as a n-butyl group, an isobutyl group, a s-butyl group, a t-butyl group, a n-pentyl group, a branched pentyl group, a secondary pentyl group, a tertiary pentyl group, a n-hexyl group, a branched hexyl group, a secondary hexyl group, a tertiary hexyl group, a n-heptyl group, a branched heptyl group, a secondary heptyl group, a tertiary heptyl group, a n-octyl group, a 2-ethylhexyl group, a branched octyl group, a secondary octyl group, a tertiary octyl group, a n-nonyl group, a branched nonyl group, a secondary nonyl group, a tertiary nonyl group, a n-decyl group, a branched decyl group, a secondary decyl group, a tertiary decyl group, a n-undecyl group, a branched undecyl group, a secondary undecyl group, a tertiary undecyl group, a n-dodecyl group, a branched dodecyl group, a secondary dodecyl group, a tertiary dodecyl group, a n-tridecyl group, a branched tridecyl group, a secondary tridecyl group, a tertiary tridecyl group, a n-tetradecyl group, a branched tetradecyl group, a secondary tetradecyl group, a tertiary tetradecyl group, a n-pentadecyl group, a branched pentadecyl group, a secondary pentadecyl group, a tertiary pentadecyl group, a n-hexadecyl group, a branched hexadecyl group, a secondary hexadecyl group, a tertiary hexadecyl group, a n-heptadecyl group, a branched heptadecyl group, a secondary heptadecyl group, a tertiary heptadecyl group, a n-octadecyl group, a branched octadecyl group, a secondary octadecyl group, a tertiary octadecyl group, a n-nonadecyl group, a branched nonadecyl group, a secondary nonadecyl group, a tertiary nonadecyl group, a n-icosyl group, a branched icosyl group, a secondary icosyl group, or a tertiary icosyl group; an unsaturated aliphatic hydrocarbon group, such as a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, a 5-hexenyl group, a 1-heptenyl group, a 6-heptenyl group, a 1-octenyl group, a 7-octenyl group, a 8-nonenyl group, a 1-decenyl group, a 9-decenyl group, a 10-undecenyl group, a 1-dodecenyl group, a 4-dodecenyl group, a 11-dodecenyl group, a 12-tridecenyl group, a 13-tetradecenyl group, a 14-pentadecenyl group, a 15-hexadecenyl group, a 16-heptadecenyl group, a 1-octadecenyl group, a 17-octadecenyl group, a 1-nonadecenyl group, or a 1-icosenyl group; an aromatic hydrocarbon group, such as a phenyl group, a toluyl group, a xylyl group, a cumenyl group, a mesityl group, a benzyl group, a phenethyl group, a styryl group, a cinnamyl group, a benzhydryl group, a trityl group, an ethylphenyl group, a propylphenyl group, a butylphenyl group, a pentylphenyl group, a hexylphenyl group, a heptylphenyl group, an octylphenyl group, a nonylphenyl group, a decylphenyl group, an undecylphenyl group, a dodecylphenyl group, a styrenated phenyl group, a p-cumylphenyl group, a phenylphenyl group, a benzylphenyl group, an α-naphthyl group, or a β-naphthyl group; and an alicyclic hydrocarbon group, such as a cyclopropyl group, a cyclobutyl group, a cyclopentyl group, a cyclohexyl group, a cycloheptyl group, a cyclooctyl group, a methylcyclopentyl group, a methylcyclohexyl group, a methylcycloheptyl group, a methylcyclooctyl group, a 4,4,6,6-tetramethylcyclohexyl group, a 1,3-dibutylcyclohexyl group, a norbornyl group, a bicyclo[2.2.2]octyl group, an adamantyl group, a 1-cyclobutenyl group, a 1-cyclopentenyl group, a 3-cyclopentenyl group, a 1-cyclohexenyl group, a 3-cyclohexenyl group, a 3-cycloheptenyl group, a 4-cyclooctenyl group, a 2-methyl-3-cyclohexenyl group, or a 3,4-dimethyl-3-cyclohexenyl group. $R^{17}$ and $R^{18}$ may be identical to each other, or may be different from each other. Of those, from the viewpoints of obtaining a compound with which the effect of the present invention is easily obtained, and easily achieving procurement and production, $R^{17}$ and $R^{18}$ each represent preferably a saturated aliphatic hydrocarbon group or an unsaturated aliphatic hydrocarbon group, more preferably a saturated aliphatic hydrocarbon group, still more preferably a saturated aliphatic hydrocarbon group having 5 to 18 carbon atoms, even more preferably a saturated aliphatic hydrocarbon group having 8 to 15 carbon atoms, most preferably a saturated aliphatic hydrocarbon group having 10 to 12 carbon atoms.

In the general formula (3), $R^{19}$ represents a divalent hydrocarbon group having 2 to 4 carbon atoms. Examples of such group include: an ethylene group; a propane-1,3-diyl (linear propylene) group; a branched propylene group, such as a propane-1,2-diyl group or a propane-2,2-diyl group; a linear butylene group, such as a butane-1,4-diyl group, a butane-1,2-diyl group, a butane-1,3-diyl group, a butane-2,3-diyl group, a butane-1,1-diyl group, or a butane-2,2-diyl group; and a branched butylene group, such as a 2-methylpropane-1,3-diyl group or a 2-methylpropane-1,2-diyl group. Of those, from the viewpoint of obtaining a compound with which the effect of the present invention is easily obtained, $R^{19}$ represents preferably a divalent linear hydrocarbon group having 2 to 4 carbon atoms, more preferably an ethylene group or a propane-1,3-diyl (linear propylene) group, still more preferably an ethylene group. $R^{19}$s may all represent identical groups, or may represent different groups.

In the general formula (3), r represents a number of 10 to 100. Of those, from the viewpoint of the ease of production or obtainment, the number is preferably from 12 to 50, more preferably from 15 to 30.

In the general formula (4), $R^{20}$ represents a divalent hydrocarbon group having 2 to 4 carbon atoms. Examples of such group include: an ethylene group; a propane-1,3-diyl (linear propylene) group; a branched propylene group, such as a propane-1,2-diyl group or a propane-2,2-diyl group; a linear butylene group, such as a butane-1,4-diyl group, a butane-1,2-diyl group, a butane-1,3-diyl group, a butane-2,3-diyl group, a butane-1,1-diyl group, or a butane-2,2-diyl group; and a branched butylene group, such as a 2-methylpropane-1,3-diyl group or a 2-methylpropane-1,2-diyl group. Of those, from the viewpoint of obtaining a compound with which the effect of the present invention is easily obtained, $R^{20}$ represents preferably a divalent linear hydrocarbon group having 2 to 4 carbon atoms, more preferably an ethylene group or a propane-1,3-diyl (linear propylene) group, still more preferably an ethylene group. $R^{20}$s may all represent identical groups, or may represent different groups.

In the general formula (4), t represents a number of 100 to 500. Of those, from the viewpoint of obtaining a compound with which the effect of the present invention is easily obtained, the number is preferably from 120 to 450, more preferably from 150 to 400, still more preferably from 180 to 350, most preferably from 200 to 300.

Examples of the diisocyanate compound represented by the general formula (5) include: aliphatic diisocyanates, such as trimethylene diisocyanate, tetramethylene diisocyanate, pentamethylene diisocyanate, hexamethylene diisocyanate (HDI), 2,2-dimethylpentane diisocyanate, octamethylene diisocyanate, 2,2,4-trimethylpentane diisocyanate, nonamethylene diisocyanate, decamethylene diisocyanate, dodecamethylene diisocyanate, isophorone diisocyanate (IPDI), dicyclohexylmethane diisocyanate (hydrogenated MDI), hydrogenated xylylene diisocyanate (hydrogenated XDI), and 2,4,4(or 2,2,4)-trimethylhexamethylene diisocyanate (TMDI); and aromatic diisocyanates, such as tolylene diisocyanate (TDI), diphenylmethane diisocyanate (MDI), toluidine diisocyanate (TODI), xylylene diisocyanate (XDI), and naphthalene diisocyanate (NDI). Q in the general formula (5) may represent any divalent hydrocarbon group having 3 to 16 carbon atoms, but preferably represents a group obtained by removing two isocyanate groups from the above-exemplified diisocyanate compound. Of the diisocyanates, an aliphatic diisocyanate is preferred, trimethylene diisocyanate, tetramethylene diisocyanate, hexamethylene diisocyanate (HDI), octamethylene diisocyanate, isophorone diisocyanate (IPDI), dicyclohexylmethane diisocyanate (hydrogenated MDI), hydrogenated xylylene diisocyanate (hydrogenated XDI), and 2,4,4(or 2,2,4)-trimethylhexamethylene diisocyanate (TMDI) are more preferred, tetramethylene diisocyanate, hexamethylene diisocyanate (HDI), octamethylene diisocyanate, isophorone diisocyanate (IPDI), and dicyclohexylmethane diisocyanate (hydrogenated MDI) are still more preferred, and tetramethylene diisocyanate, hexamethylene diisocyanate (HDI), and octamethylene diisocyanate are most preferred.

$R^4$ and $R^6$ in the general formula (1) described above each independently represent a divalent hydrocarbon group having 3 to 16 carbon atoms, and more specifically, each represent preferably a group obtained by removing two isocyanate groups from the above-exemplified diisocyanate compound, more preferably a group obtained by removing two isocyanate groups from an aliphatic diisocyanate, still more preferably a group obtained by removing two isocyanate groups from any of trimethylene diisocyanate, tetramethylene diisocyanate, hexamethylene diisocyanate (HDI), octamethylene diisocyanate, isophorone diisocyanate (IPDI) and dicyclohexylmethane diisocyanate (hydrogenated MDI), hydrogenated xylylene diisocyanate (hydrogenated XDI), and 2,4,4 (or 2,2,4)-trimethylhexamethylene diisocyanate (TMDI), even more preferably a group obtained by removing two isocyanate groups from any of tetramethylene diisocyanate, hexamethylene diisocyanate (HDI), octamethylene diisocyanate, isophorone diisocyanate (IPDI), and dicyclohexylmethane diisocyanate (hydrogenated MDI). From the viewpoint of further improving the effect of the present invention, $R^4$ and $R^6$ in the general formula (1) each most preferably represent a group obtained by removing two isocyanate groups from any of tetramethylene diisocyanate, hexamethylene diisocyanate (HDI), and octamethylene diisocyanate (divalent aliphatic hydrocarbon group having 4 to 8 carbon atoms).

As a production method, for example, it is appropriate to allow 0.8 mol to 1.2 mol, preferably 0.9 mol to 1.1 mol of the polyethylene glycol represented by the general formula (4) to react with 2 mol of the diisocyanate compound represented by the general formula (5) to synthesize a prepolymer, and then add 1.8 mol to 2.2 mol, preferably 1.9 mol to 2.1 mol of the alcohol compound represented by the general formula (3) into the system, followed by a reaction. In general, it is appropriate to allow 1 mol of the polyethylene glycol represented by the general formula (4) and 2 mol of the alcohol compound represented by the general formula (3) to react with 2 mol of the diisocyanate compound represented by the general formula (5). With regard to specific reaction conditions, there is given a method involving: adding the diisocyanate compound represented by the general formula (5) and the polyethylene glycol represented by the general formula (4) into the system; allowing the mixture to react at from 60° C. to 100° C. for from 1 hour to 10 hours; then confirming the disappearance of the polyethylene glycol represented by the general formula (4); then post-adding the alcohol compound represented by the general formula (3); and further allowing the mixture to react at the same temperature for from 1 hour to 8 hours. The reaction proceeds uncatalyzed, but a catalyst may be used. Examples of the catalyst include: metal halides, such as titanium tetrachloride, hafnium chloride, zirconium chloride, aluminum chloride, gallium chloride, indium chloride, iron chloride, tin chloride, and boron fluoride; hydroxides, alcoholates, and carbonates of alkali metals and alkaline earth metals, such as sodium hydroxide, potassium hydroxide, sodium methylate, and sodium carbonate; metal oxides, such as aluminum oxide, calcium oxide, barium oxide, and sodium oxide; organic metal compounds, such as tetraisopropyl titanate, dibutyltin dichloride, dibutyltin oxide, and dibutyltin bis(2-ethylhexyl thioglycolate); and soaps, such as sodium octylate, potassium octylate, sodium laurate, and potassium laurate. It is appropriate that any one of those catalysts be used at from about 0.01 mass % to about 1 mass % with respect to the entire system.

A production method for the compound represented by the general formula (2) is not particularly limited, and the compound may be produced using any known production method without any problem, but is preferably synthesized using compounds represented by the following general formulae (6) and (7) as raw materials because such method is simple and inexpensive.

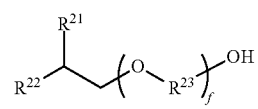

(6)

In the formula, $R^{21}$ and $R^{22}$ each independently represent a hydrocarbon group having 4 to 20 carbon atoms, $R^{23}$ represents a divalent hydrocarbon group having 2 to 4 carbon atoms, and f represents a number of 10 to 100.

OCN-T-NCO                (7)

In the formula, T represents a divalent hydrocarbon group having 3 to 16 carbon atoms.

In the general formula (6), $R^{21}$ and $R^{22}$ each independently represent a hydrocarbon group having 4 to 20 carbon atoms. Examples of such group include: a saturated aliphatic hydrocarbon group, such as a n-butyl group, an isobutyl group, a s-butyl group, a t-butyl group, a n-pentyl group, a branched pentyl group, a secondary pentyl group, a tertiary pentyl group, a n-hexyl group, a branched hexyl group, a secondary hexyl group, a tertiary hexyl group, a n-heptyl group, a branched heptyl group, a secondary heptyl group, a tertiary heptyl group, a n-octyl group, a 2-ethylhexyl group, a branched octyl group, a secondary octyl group, a tertiary octyl group, a n-nonyl group, a branched nonyl group, a secondary nonyl group, a tertiary nonyl group, a n-decyl group, a branched decyl group, a secondary decyl group, a tertiary decyl group, a n-undecyl group, a branched undecyl group, a secondary undecyl group, a tertiary undecyl group, a n-dodecyl group, a branched dodecyl group, a secondary dodecyl group, a tertiary dodecyl group, a n-tridecyl group, a branched tridecyl group, a secondary tridecyl group, a tertiary tridecyl group, a n-tetradecyl group, a branched tetradecyl group, a secondary tetradecyl group, a tertiary tetradecyl group, a n-pentadecyl group, a branched pentadecyl group, a secondary pentadecyl group, a tertiary pentadecyl group, a n-hexadecyl group, a branched hexadecyl group, a secondary hexadecyl group, a tertiary hexadecyl group, a n-heptadecyl group, a branched heptadecyl group, a secondary heptadecyl group, a tertiary heptadecyl group, a n-octadecyl group, a branched octadecyl group, a secondary octadecyl group, a tertiary octadecyl group, a n-nonadecyl group, a branched nonadecyl group, a secondary nonadecyl group, a tertiary nonadecyl group, a n-icosyl group, a branched icosyl group, a secondary icosyl group, or a tertiary icosyl group; an unsaturated aliphatic hydrocarbon group, such as a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, a 5-hexenyl group, a 1-heptenyl group, a 6-heptenyl group, a 1-octenyl group, a 7-octenyl group, a 8-nonenyl group, a 1-decenyl group, a 9-decenyl group, a 10-undecenyl group, a 1-dodecenyl group, a 4-dodecenyl group, a 11-dodecenyl group, a 12-tridecenyl group, a 13-tetradecenyl group, a 14-pentadecenyl group, a 15-hexadecenyl group, a 16-heptadecenyl group, a 1-octadecenyl group, a 17-octadecenyl group, a 1-nonadecenyl group, or a 1-icosenyl group; an aromatic hydrocarbon group, such as a phenyl group, a toluyl group, a xylyl group, a cumenyl group, a mesityl group, a benzyl group, a phenethyl group, a styryl group, a cinnamyl group, a benzhydryl group, a trityl group, an ethylphenyl group, a propylphenyl group, a butylphenyl group, a pentylphenyl group, a hexylphenyl group, a heptylphenyl group, an octylphenyl group, a nonylphenyl group, a decylphenyl group, an undecylphenyl group, a dodecylphenyl group, a styrenated phenyl group, a p-cumylphenyl group, a phenylphenyl group, a benzylphenyl group, an α-naphthyl group, or a R-naphthyl group; and an alicyclic hydrocarbon group, such as a cyclopropyl group, a cyclobutyl group, a cyclopentyl group, a cyclohexyl group, a cycloheptyl group, a cyclooctyl group, a methylcyclopentyl group, a methylcyclohexyl group, a methylcycloheptyl group, a methylcyclooctyl group, a 4,4,6,6-tetramethylcyclohexyl group, a 1,3-dibutylcyclohexyl group, a norbornyl group, a bicyclo[2.2.2]octyl group, an adamantyl group, a 1-cyclobutenyl group, a 1-cyclopentenyl group, a 3-cyclopentenyl group, a 1-cyclohexenyl group, a 3-cyclohexenyl group, a 3-cycloheptenyl group, a 4-cyclooctenyl group, a 2-methyl-3-cyclohexenyl group, or a 3,4-dimethyl-3-cyclohexenyl group. $R^{21}$ and $R^{22}$ may be identical to each other, or may be different from each other. Of those, from the viewpoints of obtaining a compound with which the effect of the present invention is easily obtained, and easily achieving procurement and production, $R^{21}$ and $R^{22}$ each represent preferably a saturated aliphatic hydrocarbon group or an unsaturated aliphatic hydrocarbon group, more preferably a saturated aliphatic hydrocarbon group, still more preferably a saturated aliphatic hydrocarbon group having 5 to 18 carbon atoms, even more preferably a saturated aliphatic hydrocarbon group having 8 to 15 carbon atoms, most preferably a saturated aliphatic hydrocarbon group having 10 to 12 carbon atoms.

In the general formula (6), $R^{23}$ represents a divalent hydrocarbon group having 2 to 4 carbon atoms. Examples of such group include: an ethylene group; a propane-1,3-diyl (linear propylene) group; a branched propylene group, such as a propane-1,2-diyl group or a propane-2,2-diyl group; a linear butylene group, such as a butane-1,4-diyl group, a butane-1,2-diyl group, a butane-1,3-diyl group, a butane-2,3-diyl group, a butane-1,1-diyl group, or a butane-2,2-diyl group; and a branched butylene group, such as a 2-methylpropane-1,3-diyl group or a 2-methylpropane-1,2-diyl group. Of those, from the viewpoint of obtaining a compound with which the effect of the present invention is easily obtained, $R^{23}$ represents preferably a divalent linear hydrocarbon group having 2 to 4 carbon atoms, more preferably an ethylene group or a propane-1,3-diyl (linear propylene) group, still more preferably an ethylene group. $R^{23}$s may all represent identical groups, or may represent different groups.

In the general formula (6), f represents a number of 10 to 100. Of those, from the viewpoint of the ease of production or obtainment, the number is preferably from 12 to 50, more preferably from 15 to 30.

Examples of the diisocyanate compound represented by the general formula (7) include: aliphatic diisocyanates, such as trimethylene diisocyanate, tetramethylene diisocyanate, pentamethylene diisocyanate, hexamethylene diisocyanate (HDI), 2,2-dimethylpentane diisocyanate, octamethylene diisocyanate, 2,2,4-trimethylpentane diisocyanate, nonamethylene diisocyanate, decamethylene diisocyanate, dodecamethylene diisocyanate, isophorone diisocyanate (IPDI), dicyclohexylmethane diisocyanate (hydrogenated MDI), hydrogenated xylylene diisocyanate (hydrogenated XDI), and 2,4,4 (or 2,2,4)-trimethylhexamethylene diisocyanate (TMDI); and aromatic diisocyanates, such as tolylene diisocyanate (TDI), diphenylmethane diisocyanate (MDI), toluidine diisocyanate (TODI), xylylene diisocyanate (XDI), and naphthalene diisocyanate (NDI). T in the general formula (7) may represent any divalent hydrocarbon group having 3 to 16 carbon atoms, but preferably represents a group obtained by removing two isocyanate groups from the above-exemplified diisocyanate compound. Of the diisocyanates, an aliphatic diisocyanate is preferred, trimethylene diisocyanate, tetramethylene diisocyanate, hexamethylene diisocyanate (HDI), octamethylene diisocyanate, isophorone diisocyanate (IPDI), dicyclohexylmethane diisocyanate (hydrogenated MDI), hydrogenated xylylene diisocyanate (hydrogenated XDI), and 2,4,4 (or 2,2,4)-trimethylhexamethylene diisocyanate (TMDI) are more preferred, tetramethylene diisocyanate, hexamethylene diisocyanate (HDI), octamethylene diisocyanate, isophorone diisocyanate (IPDI), and dicyclohexylmethane diisocyanate (hydrogenated MDI) are still more preferred, and tetramethylene diisocyanate, hexamethylene diisocyanate (HDI), and octamethylene diisocyanate are most preferred.

$R^{13}$ in the general formula (2) described above represents a divalent hydrocarbon group having 3 to 16 carbon atoms, and more specifically, each represent preferably a group obtained by removing two isocyanate groups from the above-exemplified diisocyanate compound, more preferably a group obtained by removing two isocyanate groups from an aliphatic diisocyanate, still more preferably a group obtained by removing two isocyanate groups from any of trimethylene diisocyanate, tetramethylene diisocyanate, hexamethylene diisocyanate (HDI), octamethylene diisocyanate, isophorone diisocyanate (IPDI) and dicyclohexylmethane diisocyanate (hydrogenated MDI), hydrogenated xylylene diisocyanate (hydrogenated XDI), and 2,4,4 (or 2,2,4)-trimethylhexamethylene diisocyanate (TMDI), even more preferably a group obtained by removing two isocyanate groups from any of tetramethylene diisocyanate, hexamethylene diisocyanate (HDI), octamethylene diisocyanate, isophorone diisocyanate (IPDI), and dicyclohexylmethane diisocyanate (hydrogenated MDI). From the viewpoint of further improving the effect of the present invention, $R^{13}$ in the general formula (2) most preferably represents a group obtained by removing two isocyanate groups from any of tetramethylene diisocyanate, hexamethylene diisocyanate (HDI), and octamethylene diisocyanate (divalent aliphatic hydrocarbon group having 4 to 8 carbon atoms).

As a production method, for example, it is appropriate to allow 1.8 mol to 2.2 mol, preferably 1.9 mol to 2.1 mol of the alcohol compound represented by the general formula (6) to react with 1 mol of the diisocyanate compound represented by the general formula (7). In general, it is appropriate to allow 2 mol of the alcohol compound represented by the general formula (6) to react with 1 mol of the diisocyanate compound represented by the general formula (7). With regard to specific reaction conditions, there is given a method involving adding the diisocyanate compound represented by the general formula (7) and the alcohol compound represented by the general formula (6) into the system, and allowing the mixture to react at from 60° C. to 100° C. for from 1 hour to 10 hours. The reaction proceeds uncatalyzed, but a catalyst may be used. Examples of the catalyst include: metal halides, such as titanium tetrachloride, hafnium chloride, zirconium chloride, aluminum chloride, gallium chloride, indium chloride, iron chloride, tin chloride, and boron fluoride; hydroxides, alcoholates, and carbonates of alkali metals and alkaline earth metals, such as sodium hydroxide, potassium hydroxide, sodium methylate, and sodium carbonate; metal oxides, such as aluminum oxide, calcium oxide, barium oxide, and sodium oxide; organic metal compounds, such as tetraisopropyl titanate, dibutyltin dichloride, dibutyltin oxide, and dibutyltin bis(2-ethylhexyl thioglycolate); and soaps, such as sodium octylate, potassium octylate, sodium laurate, and potassium laurate. It is appropriate that any one of those catalysts be used at from about 0.01 mass % to about 1 mass % with respect to the entire system.

Unless the aqueous gelling agent composition of the present invention contains compound (A) represented by the general formula (1) and compound (B) represented by the general formula (2) and the mass ratio of compound (A) to compound (B), (A):(B), is from 95:5 to 85:15, an aqueous gelling agent composition exhibiting the effect of the present invention is not obtained. Of those, from the viewpoint that the effect of the present invention is remarkably exhibited, the mass ratio of compound (A) to compound (B), (A):(B), is preferably from 94:6 to 87:13, the mass ratio (A):(B) is more preferably from 93:7 to 89:11, and the mass ratio (A):(B) is still more preferably from 92:8 to 90:10. When the mass ratio of (B) is below the range of (A):(B)=95:5, it is difficult to obtain an elastic and soft gel by adding the aqueous gelling agent composition to water unless a large amount of the aqueous gelling agent is used, and a sufficient self-leveling property is also not obtained. In addition, when the mass ratio of (B) is above the range of (A):(B)=85:15, the addition of the aqueous gelling agent composition to water results in a cloudy sol state, and a gel is not obtained.

The aqueous gelling agent composition of the present invention is preferably produced by synthesizing each of compound (A) represented by the general formula (1) and compound (B) represented by the general formula (2), and mixing compound (A) and compound (B) with each other so that the mass ratio (A):(B) may be from 95:5 to 85:15. In this case, when the raw materials for producing compound (A) represented by the general formula (1) and the raw materials for producing compound (B) represented by the general formula (2) are allowed to react in the same system, there is obtained a product having mixed therein compound (A) represented by the general formula (1) and compound (B) represented by the general formula (2). However, in such method, it is extremely difficult to perform the production so that the mass ratio of compound (A) to compound (B), (A):(B), may be from 95:5 to 85:15, and the setting of reaction conditions is very difficult. In general, when the aqueous gelling agent composition is produced by such method, compound (B) is produced in an amount of less than 5 mass % or more than 15 mass % with respect to the entirety of the aqueous gelling agent composition. Accordingly, the aqueous gelling agent composition obtained by such method does not have a mass ratio of compound (A) to compound (B), (A):(B), within the range of from 95:5 to 85:15, and hence an aqueous gelling agent exhibiting the effect of the present invention cannot be obtained. The conversion of such product into an aqueous gelling agent composition exhibiting the effect of the present invention requires a time- and labor-consuming process of analyzing the production amounts of compound (A) and compound (B) in the obtained product, and post-adding compound (A) or compound (B) to the product so that the mass ratio of compound (A) to compound (B), (A):(B), may be from 95:5 to 85:15, and hence is not preferred. The mass ratio of compound (A) to compound (B) in the aqueous gelling agent composition after production may be analyzed by gel permeation chromatography.

Each of compound (A) and compound (B), which constitute the aqueous gelling agent composition of the present invention, is a solid or a viscous substance at room temperature. The aqueous gelling agent composition of the present invention is a mixture of compound (A) and compound (B), and hence is preferably brought into a liquid state by being dissolved in a solvent, such as water, in advance, in order to achieve a uniform product state. The amount of the solvent is not particularly specified, but from the viewpoint of the ease of handling, is preferably adjusted so that the concentration of the aqueous gelling agent composition of the present invention may be from 10 mass % to 50 mass %, more preferably from 15 mass % to 40 mass %.

Examples of the solvent that may be used include: water; and volatile primary alcohol compounds, such as methanol, ethanol, and propanol. Of those, water is most preferred because volatile solvents may be restricted depending on the site of use.

In addition, from the viewpoint of enhancing the self-leveling property of the aqueous gel to be obtained, the aqueous gelling agent composition of the present invention preferably uses a polyol compound in combination with water. Examples of such polyol compound include ethylene glycol, propylene glycol, butylene glycol, glycerol, diethylene glycol, dipropylene glycol, polyethylene glycol, and a sugar alcohol. Of those, from the viewpoint that the self-leveling property is remarkably exhibited, propylene glycol, butylene glycol, or diethylene glycol is preferred, butylene glycol or diethylene glycol is more preferred, and butylene glycol is still more preferred. When any such polyol compound is used in combination with water, it is preferred that 5 parts by mass to 250 parts by mass of the polyol compound be added with respect to 100 parts by mass of water.

The aqueous gelling agent composition of the present invention is preferably blended at from 0.1 part by mass to 5 parts by mass with respect to 100 parts by mass of the total amount of the solvent (such as water) and the polyol compound because an aqueous gel exhibiting the effect of the present invention is easily formed. In addition, from the viewpoint that an aqueous gel exhibiting the effect of the present invention is more easily formed, the aqueous gelling agent composition of the present invention is more preferably blended at from 0.2 part by mass to 3 parts by mass, still more preferably blended at from 0.5 part by mass to 1 part by mass, with respect to 100 parts by mass of the total amount of the solvent (such as water) and the polyol compound. When the blending amount of the aqueous gelling agent composition of the present invention is less than 0.1 part by mass, a gel cannot be formed in some cases or the effect of the present invention is not obtained in some cases. Also when the blending amount is more than 5 parts by mass, a gel cannot be formed in some cases or the effect of the present invention is not obtained in some cases. As described in detail later, the aqueous gelling agent composition of the present invention may be used with other additives generally used in aqueous cosmetics within a qualitative and quantitative range in which the effect of the present invention is not impaired. Also when the aqueous gelling agent composition of the present invention is added to an aqueous cosmetic using such additives, the aqueous gelling agent composition is preferably blended at from 0.1 part by mass to 5 parts by mass with respect to 100 parts by mass of the total amount of the solvent (such as water) and the polyol compound in the aqueous cosmetic, and from the viewpoint of facilitating the obtaining of an aqueous cosmetic exhibiting the effect of the present invention, is more preferably blended at from 0.2 part by mass to 3 parts by mass, still more preferably blended at from 0.5 part by mass to 1 part by mass.

The aqueous gelling agent composition of the present invention may be used for any product in an application in which the viscosity of an aqueous solution is modified. Examples of such product include an aqueous paint, an aqueous adhesive, an aqueous detergent, and an aqueous cosmetic. Of those, from the viewpoint that gel properties of having a self-leveling property and being usable with a spray bottle, which are the effect of the present invention, are strongly desired, the aqueous gelling agent composition of the present invention is preferably used in an aqueous cosmetic application, more preferably used in a basic cosmetic application, such as a face lotion, a milky lotion, a beauty serum, or a cream, among aqueous cosmetics, still more preferably used in a "two-in-one cosmetic" or "all-in-one cosmetic" application. The "all-in-one cosmetic" is as described below: while in general, as kinds of the basic cosmetic, there are given face lotions, milky lotions, beauty serums, creams, and the like, each of which plays a different role, the "all-in-one cosmetic" refers to a very highly functional and convenient cosmetic that allows those roles to be covered by one cosmetic. In addition, in particular, a cosmetic having both the two roles of the face lotion and the milky lotion or the like is sometimes referred to as "two-in-one cosmetic".

For the aqueous cosmetic containing the aqueous gelling agent composition of the present invention, other additives generally used in cosmetic compositions may be used for the purpose of imparting various characteristics as appropriate within a qualitative and quantitative range in which the effect of the present invention is not impaired. Examples thereof include a powder component, a liquid oil and fat, a solid oil and fat, wax, a hydrocarbon oil, a higher fatty acid, an anionic surfactant, a cationic surfactant, an amphoteric surfactant, a nonionic surfactant, a moisturizing agent, a water-soluble polymer compound, a sequestering agent, a sugar, an amino acid and derivatives thereof, an organic amine, a pH adjustor, a vitamin, an antioxidant, a preservative, a circulation promoter, an antiphlogistic agent, an activator, a whitening agent, an antiseborrheic agent, an anti-inflammatory agent, and various extracts. One kind or two or more kinds thereof may be arbitrarily blended.

Examples of the powder component include: inorganic powders (for example, talc, kaolin, mica, sericite, white mica, bronze mica, synthetic mica, lepidolite, black mica, vermiculite, magnesium carbonate, calcium carbonate, aluminum silicate, barium silicate, calcium silicate, magnesium silicate, strontium silicate, a metal salt of tungstic acid, magnesium, silica, zeolite, barium sulfate, calcined calcium sulfate (calcined gypsum), calcium phosphate, fluorine apatite, hydroxyapatite, ceramic powder, metal soap (for example, zinc myristate, calcium palmitate, or aluminum stearate), and boron nitride); organic powders (for example, polyamide resin powder (nylon powder), polyethylene powder, polymethyl methacrylate powder, polystyrene powder, copolymer resin powder of styrene and acrylic acid, benzoguanamine resin powder, polytetrafluoroethylene powder, and cellulose powder); inorganic white pigments (for example, titanium dioxide and zinc oxide); inorganic red pigments (for example, iron oxide (red iron oxide) and iron titanate); inorganic brown pigments (for example, γ-iron oxide); inorganic yellow pigments (for example, yellow iron oxide and yellow ocher); inorganic black pigments (for example, black iron oxide and lower titanium oxide); inorganic purple pigments (for example, manganese violet and cobalt violet); inorganic green pigments (for example, chromium oxide, chromium hydroxide, and cobalt titanate); inorganic blue pigments (for example, ultramarine blue and Prussian blue); pearl pigments (for example, titanium oxide-coated mica, titanium oxide-coated bismuth oxychloride, titanium oxide-coated talc, colored titanium oxide-coated mica, bismuth oxychloride, and argentine); metal powder pigments (for example, aluminum powder and copper powder); organic pigments, such as zirconium, barium, and an aluminum lake (for example, organic pigments, such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, and Blue No. 404, and Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1); and natural colorants (for example, chlorophyl and R-carotene).

Examples of the liquid oil and fat include avocado oil, camellia oil, turtle oil, macadamia nut oil, corn oil, mink oil, olive oil, rapeseed oil, egg-yolk oil, sesame oil, persic oil, wheat germ oil, sasanqua oil, castor oil, linseed oil, safflower oil, cottonseed oil, perilla oil, soybean oil, peanut oil, tea seed oil, kaya oil, rice bran oil, paulownia oil, Japan tung oil, jojoba oil, germ oil, and triglycerin.

Examples of the solid oil and fat include cacao butter, coconut oil, hydrogenated coconut oil, palm oil, palm kernel oil, Japan wax kernel oil, hydrogenated oil, Japan wax, and hydrogenated castor oil.

Examples of the wax include beeswax, candelilla wax, cotton wax, carnauba wax, bayberry wax, privet wax, whale wax, montan wax, bran wax, lanolin, kapok wax, lanolin acetate, liquid lanolin, sugar cane wax, a lanolin fatty acid isopropyl ester, hexyl laurate, reduced lanolin, jojoba wax, hard lanolin, shellac wax, a POE lanolin alcohol ether, a POE lanolin alcohol acetate, a POE cholesterol ether, a lanolin fatty acid polyethylene glycol, and a POE hydrogenated lanolin alcohol ether.

Examples of the hydrocarbon oil include liquid paraffin, ozocerite, squalane, pristane, paraffin, ceresin, squalene, vaseline, and microcrystalline wax.

Examples of the higher fatty acid include lauric acid, myristic acid, palmitic acid, stearic acid, behenic acid, oleic acid, undecylenic acid, a tall oil fatty acid, isostearic acid, linoleic acid, linolenic acid, eicosapentaenoic acid (EPA), and docosahexaenoic acid (DHA).

Examples of the anionic surfactant include: fatty acid soaps (such as sodium laurate and sodium palmitate); higher alkyl sulfate ester salts (such as sodium lauryl sulfate and potassium lauryl sulfate); alkyl ether sulfate ester salts (such as POE-lauryl sulfate triethanolamine and POE-sodium lauryl sulfate); N-acylsarcosinates (such as sodium lauroylsarcosine); higher fatty acid amide sulfonic acid salts (such as N-myristoyl-N-methyl taurine sodium, a coconut oil fatty acid methyl taurine sodium, and lauryl methyl taurine sodium); phosphate ester salts (POE-sodium oleylether phosphate, POE-stearyl ether phosphate, and the like); sulfosuccinic acid salts (such as sodium di-2-ethylhexyl sulfosuccinate, sodium monolauroyl monoethanolamide polyoxyethylene sulfosuccinate, and sodium lauryl polypropylene glycol sulfosuccinate); alkyl benzenesulfonic acid salts (such as linear sodium dodecylbenzenesulfonate, linear triethanolamine dodecylbenzenesulfonate, and linear dodecylbenzenesulfonic acid); higher fatty acid ester sulfate ester salts (such as a hydrogenated coconut oil fatty acid glycerin sodium sulfate); N-acyl glutamic acid salts (such as monosodium N-lauroyl glutamate, disodium N-stearoyl glutamate, and monosodium N-myristoyl-L-glutamate); sulfonated oils (such as Turkey red oil); POE-alkyl ether carboxylic acids; POE-alkylallyl ether carboxylic acid salts; α-olefinsulfonic acid salts; higher fatty acid ester sulfonic acid salts; secondary alcohol sulfate ester salts; higher fatty acid alkylolamide sulfate ester salts; sodium lauroyl monoethanolamide succinate; N-palmitoyl aspartate ditriethanolamine; and casein sodium.

Examples of the cationic surfactant include: alkyltrimethylammonium salts (such as stearyltrimethylammonium chloride and lauryltrimethylammonium chloride); alkylpyridinium salts (such as cetylpyridinium chloride); a distearyldimethylammonium dialkyldimethylammonium chloride salt; poly(N,N'-dimethyl-3,5-methylenepiperidinium) chloride; an alkyl quaternary ammonium salt; an alkyldimethylbenzylammonium salt; an alkylisoquinolinium salt; a dialkylmorpholinium salt; a POE-alkylamine; an alkylamine salt; a polyamine fatty acid derivative; an amyl alcohol fatty acid derivative; benzalkonium chloride; and benzethonium chloride.

Examples of the amphoteric surfactant include: imidazoline-based amphoteric surfactants (such as sodium 2-undecyl-N,N,N-(hydroxyethylcarboxymethyl)-2-imidazoline, and 2-cocoyl-2-imidazolium hydroxide-1-carboxyethyloxy disodium salt); and betaine-based surfactants (such as 2-heptadecyl-N-carboxymethyl-N-hydroxyethylimidazolium betaine, betaine lauryldimethylaminoacetate, an alkylbetaine, amidobetaine, and sulfobetaine).

Examples of the nonionic surfactant include: sorbitan fatty acid esters (such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate); glycerin polyglycerin fatty acids (such as a monocottonseed oil fatty acid glycerin, glycerin monoerucate, glycerin sesquioleate, glycerin monostearate, glycerin α,α'-oleate pyroglutamate, and glycerin monostearate malate); propylene glycol fatty acid esters (such as propylene glycol monostearate); a hydrogenated castor oil derivative; a glycerin alkyl ether; POE-sorbitan fatty acid esters (such as POE-sorbitanmonooleate, POE-sorbitanmonostearate, POE-sorbitan monooleate, and POE-sorbitan tetraoleate); POE-sorbit fatty acid esters (such as POE-sorbit monolaurate, POE-sorbit monooleate, POE-sorbit pentaoleate, and POE-sorbit monostearate); POE-glycerin fatty acid esters (such as POE-monooleates, e.g., POE-glycerin monostearate, POE-glycerin monoisostearate, and POE-glycerin triisostearate); POE-fatty acid esters (such as POE-distearate, POE-monodioleate, and ethylene glycol distearate); POE-alkyl ethers (such as POE-lauryl ether, POE-oleyl ether, POE-stearyl ether, POE-behenyl ether, POE-2-octyldodecyl ether, and POE-cholestanol ether); Pluronic-type surfactants (such as Pluronic); POE/POP-alkyl ethers (such as POE/POP-cetyl ether, POE/POP-2-decyltetradecyl ether, POE/POP-monobutyl ether, POE/POP-hydrogenated lanolin, and POE/POP-glycerin ether); tetra POE/tetra POP-ethylenediamine condensates (such as Tetronic); POE-castor oil/hydrogenated castor oil derivatives (such as POE-castor oil, POE-hydrogenated castor oil, POE-hydrogenated castor oil monoisostearate, POE-hydrogenated castor oil triisostearate, POE-hydrogenated castor oil monopyroglutamic acid monoisostearic acid diester, and POE-hydrogenated castor oil maleic acid ester); a POE-beeswax/lanolin derivative (such as POE-sorbit beeswax); alkanolamides (such as a coconut oil fatty acid diethanolamide, lauric acid monoethanol amide, and a fatty acid isopropanolamide); a POE-propylene glycol fatty acid ester; a POE-alkylamine; a POE-fatty acid amide; a sucrose fatty acid ester; an alkylethoxydimethylamine oxide; and trioleyl phosphate.

Examples of the moisturizing agent include polyethylene glycol, xylitol, sorbitol, maltitol, chondroitin sulfate, hyaluronic acid, mucoitin sulfate, charonic acid, atelocollagen, cholesteryl-12-hydroxystearate, sodium lactate, a bile acid salt, a dl-pyrrolidonecarboxylic acid salt, short-chain soluble collagen, a diglycerin (EO)PO adduct, a rosa roxburghii extract, a yarrow extract, and a sweet clover extract.

Examples of the water-soluble polymer compound include: starch-based polymers (such as carboxymethyl starch and methylhydroxypropyl starch); cellulose-based polymers (such as methylcellulose, ethylcellulose, methylhydroxypropylcellulose, hydroxyethylcellulose, sodium cellulose sulfate, hydroxypropylcellulose, carboxymethylcellulose, sodium carboxymethylcellulose, crystalline cellulose, and cellulose powder); alginic acid-based polymers (such as sodium alginate and propylene glycol alginate ester); vinyl-based polymers (such as polyvinyl alcohol, polyvinyl methyl ether, polyvinylpyrrolidone, and a carboxyvinyl polymer); polyoxyethylene-based polymers (such as polyoxyethylene-polyoxypropylene copolymers of polyethylene glycol 20,000, 40,000, or 60,000); acrylic polymers (such as sodium polyacrylate, polyethyl acrylate, and polyacrylamide); polyethylene imine; and cationic polymers.

Examples of the sequestering agent include 1-hydroxyethane-1,1-diphosphonic acid, 1-hydroxyethane-1,1-diphosphonic acid tetrasodium salt, disodium edetate, trisodium edetate, tetrasodium edetate, sodium citrate, sodium polyphosphate, sodium metaphosphate, gluconic acid, phosphoric acid, citric acid, ascorbic acid, succinic acid, edetic acid, and trisodium ethylenediamine hydroxyethyl triacetate.

As a monosaccharide, there are given, for example: trioses (such as D-glyceryl aldehyde and dihydroxyacetone); tetroses (such as D-erythrose, D-erythrulose, D-threose, and erythritol); pentoses (such as L-arabinose, D-xylose, L-lixose, D-arabinose, D-ribose, D-ribulose, D-xylulose, and L-xylulose); hexoses (such as D-glucose, D-talose, D-psicose, D-galactose, D-fructose, L-galactose, L-mannose, and D-tagatose); heptoses (such as aldoheptose and heptulose); octoses (such as octulose); deoxy sugars (such as 2-deoxy-D-ribose, 6-deoxy-L-galactose, and 6-deoxy-L-mannose); amino acids (such as D-glucosamine, D-galactosamine, sialic acid, amino uronic acid, and muramic acid); and uronic acids (such as D-glucuronic acid, D-mannuronic acid, L-guluronic acid, D-galacturonic acid, and L-iduronic acid)

As an oligosaccharide, there are given, for example, sucrose, umbelliferose, lactose, planteose, isolychnoses, α,α-trehalose, raffinose, lychnoses, umbilicin, and stachyose-verbascoses.

As a polysaccharide, there are given, for example, cellulose, quince seed, chondroitin sulfate, starch, galactan, dermatan sulfate, glycogen, gum arabic, heparan sulfate, hyaluronic acid, gum tragacanth, keratan sulfate, chondroitin, xanthane gum, mucoitin sulfate, guar gum, dextran, keratosulfate, locust bean gum, succinoglucan, and charonic acid.

Examples of the amino acid include: neutral amino acids (such as threonine and cysteine); and basic amino acids (such as hydroxylysine). In addition, as an amino acid derivative, there are given, for example, acylsarcosine sodium (lauroylsarcosine sodium), acylglutamic acid salts, acyl R-alanine sodium, glutathione, and pyrrolidone carboxylic acid.

Examples of the organic amine include monoethanolamine, diethanolamine, triethanolamine, morpholine, triisopropanolamine, 2-amino-2-methyl-1,3-propanediol, and 2-amino-2-methyl-1-propanol.

Examples of the pH adjustor include buffers, such as lactic acid-sodium lactate, citric acid-sodium citrate, and succinic acid-sodium succinate.

Examples of the vitamin include vitamins A, B1, B2, B6, C, and E and derivatives thereof, pantothenic acid and derivatives thereof, and biotin.

Examples of the antioxidant include tocopherols, dibutylhydroxytoluene, butylhydroxyanisole, and gallic acid esters.

As other blendable components, there are given, for example: preservatives (such as methylparaben, ethylparaben, butylparaben, and phenoxyethanol); antiphlogistic agents (such as glycyrrhizic acid derivatives, glycyrrhetinic acid derivatives, salicylic acid derivatives, hinokitiol, zinc oxide, and allantoin); whitening agents (such as a saxifrage extract and arbutin); various extracts (extracts of Phellodendron bark, Coptis japonica, lithospermum root, Paeonia lactiflora, Swertia japonica, birch, sage, loquat, carrot, aloe, mallow, iris, grapevine, coix seed, dishcloth gourd, lily, saffron, Cnidium rhizome, ginger, hypericum, Ononis spinosa, garlic, capsicum, Citrus Unshiu Peel, Angelica acutiloba, seaweed, or the like); activators (such as royal jelly, a photosensitive element, and cholesterol derivatives); circulation promoters (such as benzyl nicotinate, R-butoxyethyl nicotinate, capsaicin, zingerone, Cantharides tincture, ichthammol, tannic acid, α-borneol, tocopherol nicotinate, inositol hexanicotinate, cyclandelate, cinnarizine, tolazoline, acetylcholine, verapamil, cepharanthine, and γ-orizanol); antiseborrheic agents (such as sulfur and thianthol); and anti-inflammatory agents (such as tranexamic acid, thiotaurine, and hypotaurine).

EXAMPLES

The present invention is hereinafter described in more detail by way of Examples. However, the present invention is by no means limited by these examples, and modifications may be made without departing from the scope of the present invention. In the following Examples and the like, % is by mass unless otherwise stated.

Raw materials used in the production of the aqueous gelling agent composition of the present invention are described below.

<Raw Materials Used in Production of Compound (A) Represented by General Formula (1)>

Compound (3)-1: Compound of the general formula (3), where $R^{17}$=decyl group, $R^{18}$=dodecyl group, $R^{19}$=ethylene group, and r=20

Compound (3)-2: Compound of the general formula (3), where $R^{17}$=hexyl group, $R^{18}$=octyl group, $R^{19}$=ethylene group, and r=20

Compound (3)-3: Compound of the general formula (3), where $R^{17}$=octyl group, $R^{18}$=decyl group, $R^{19}$=ethylene group, and r=20

Compound (3)-4: Compound of the general formula (3), where $R^{17}$=dodecyl group, $R^{18}$=tetradecyl group, $R^{19}$=ethylene group, and r=20

Compound (3)-5: Compound of the general formula (3), where $R^{17}$=tetradecyl group, $R^{18}$=hexadecyl group, $R^{19}$=ethylene group, and r=20

Compound (3)-6: Compound of the general formula (3), where $R^{17}$=decyl group, $R^{18}$=dodecyl group, $R^{19}$=ethylene group, and r=100

Compound (4)-1: Compound of the general formula (4), where $R^{20}$=ethylene group and t=240

Compound (4)-2: Compound of the general formula (4), where $R^{20}$=ethylene group and t=450

Compound (5)-1: Hexamethylene diisocyanate

Compound (5)-2: Dicyclohexylmethane diisocyanate (hydrogenated MDI)

Compound (5)-3: Isophorone diisocyanate (IPDI)

<Raw Materials Used in Production of Compound (B) Represented by General Formula (2)>

Compound (6)-i: Compound of the general formula (6), where $R^{21}$=decyl group, $R^{22}$=dodecyl group, $R^{23}$=ethylene group, and f=20

Compound (6)-2: Compound of the general formula (6), where $R^{21}$=hexyl group, $R^{22}$=octyl group, $R^{23}$=ethylene group, and f=20

Compound (6)-3: Compound of the general formula (6), where $R^{21}$=octyl group, $R^{22}$=decyl group, $R^{23}$=ethylene group, and f=20

Compound (6)-4: Compound of the general formula (6), where $R^{21}$=dodecyl group, $R^{22}$=tetradecyl group, $R^{23}$=ethylene group, and f=20

Compound (6)-5: Compound of the general formula (6), where $R^{21}$=tetradecyl group, $R^{22}$=hexadecyl group, $R^{23}$=ethylene group, and f=20

Compound (6)-6: Compound of the general formula (6), where $R^{21}$=decyl group, $R^{22}$=dodecyl group, $R^{23}$=ethylene group, and f=100

Compound (7)-1: Hexamethylene diisocyanate

Compound (7)-2: Dicyclohexylmethane diisocyanate (hydrogenated MDI)

Compound (7)-3: Isophorone diisocyanate (IPDI)

Compound (A) represented by the general formula (1) and compound (B) represented by the general formula (2) were produced by using the raw materials above.

<Production of Compound (A) Represented by General Formula (1)>

402.2 g (0.0348 mol) of compound (4)-1 was loaded into a 1,000 ml volume four-necked flask with a thermometer, a nitrogen introducing pipe, and a stirring machine, and the temperature was increased to from 50° C. to 60° C. to melt compound (4)-1. After that, 11.7 g (0.0697 mol) of compound (5)-1 was loaded, and the inside of the system was purged with nitrogen. The components were stirred to uniformity. After it had been confirmed that the components were uniformly mixed with each other, the temperature was further increased to from 70° C. to 80° C., and the mixture was allowed to react at the same temperature for 3 hours. After that, 86.1 g (0.0697 mol) of compound (3)-1 was added into the system, and the mixture was further allowed to react at from 70° C. to 80° C. for 6 hours to afford compound (A)-1.

Further, compounds (A)-2 to (A)-9 were produced by the same method using raw materials shown in Table 1.

TABLE 1

| | Type of raw material | | | Amount of raw material used (mol) | | |
|---|---|---|---|---|---|---|
| | Compound (3) | Compound (4) | Compound (5) | Compound (3) | Compound (4) | Compound (5) |
| Compound (A)-1 | Compound (3)-1 | Compound (4)-1 | Compound (5)-1 | 0.0697 | 0.0348 | 0.0697 |
| Compound (A)-2 | Compound (3)-2 | Compound (4)-1 | Compound (5)-1 | 0.0708 | 0.0354 | 0.0708 |
| Compound (A)-3 | Compound (3)-3 | Compound (4)-1 | Compound (5)-1 | 0.0702 | 0.0351 | 0.0702 |
| Compound (A)-4 | Compound (3)-4 | Compound (4)-1 | Compound (5)-1 | 0.0691 | 0.0346 | 0.0691 |
| Compound (A)-5 | Compound (3)-5 | Compound (4)-1 | Compound (5)-1 | 0.0686 | 0.0343 | 0.0686 |
| Compound (A)-6 | Compound (3)-6 | Compound (4)-1 | Compound (5)-1 | 0.0467 | 0.0234 | 0.0467 |
| Compound (A)-7 | Compound (3)-1 | Compound (4)-2 | Compound (5)-1 | 0.0442 | 0.0221 | 0.0442 |
| Compound (A)-8 | Compound (3)-1 | Compound (4)-1 | Compound (5)-2 | 0.0688 | 0.0344 | 0.0688 |
| Compound (A)-9 | Compound (3)-1 | Compound (4)-1 | Compound (5)-3 | 0.0692 | 0.0346 | 0.0692 |

<Production of Compound (B) Represented by General Formula (2)>

468.1 g (0.38 mol) of compound (6)-1 was loaded into a 1,000 ml volume four-necked flask with a thermometer, a nitrogen introducing pipe, and a stirring machine, and the temperature was increased to from 50° C. to 60° C. to melt compound (6)-1. After that, 39.1 g (0.19 mol) of compound (7)-1 was loaded, and the inside of the system was purged with nitrogen. The components were stirred to uniformity. After it had been confirmed that the components were uniformly mixed with each other, the temperature was further increased to from 70° C. to 80° C., and the mixture was allowed to react at the same temperature for 6 hours to afford compound (B)-1.

Further, compounds (B)-2 to (B)-8 were produced by the same method using raw materials shown in Table 2.

TABLE 2

| | Type of raw material | | Amount of raw material used (mol) | |
|---|---|---|---|---|
| | Compound (6) | Compound (7) | Compound (6) | Compound (7) |
| Compound (B)-1 | Compound (6)-1 | Compound (7)-1 | 0.3788 | 0.1894 |
| Compound (B)-2 | Compound (6)-2 | Compound (7)-1 | 0.4140 | 0.2070 |
| Compound (B)-3 | Compound (6)-3 | Compound (7)-1 | 0.3957 | 0.1978 |
| Compound (B)-4 | Compound (6)-4 | Compound (7)-1 | 0.3634 | 0.1817 |
| Compound (B)-5 | Compound (6)-5 | Compound (7)-1 | 0.3492 | 0.1746 |
| Compound (B)-6 | Compound (6)-6 | Compound (7)-1 | 0.1033 | 0.0517 |
| Compound (B)-7 | Compound (6)-1 | Compound (7)-2 | 0.3658 | 0.1829 |
| Compound (B)-8 | Compound (6)-1 | Compound (7)-3 | 0.3712 | 0.1856 |

The produced compound (A) and compound (B) were mixed with each other to prepare an aqueous gelling agent composition shown in Table 3. Those aqueous gelling agent compositions are each a solution having a solid content of 30% diluted with water and butylene glycol (BG) in order to uniformly mix compound (A) and compound (B) with each other. The mass ratios of compound (A) and compound (B) in the aqueous gelling agent compositions shown in Table 3 were confirmed by performing measurement through the use of gel permeation chromatography (GPC) and finding area ratios in the resultant chart. Detailed measurement conditions are as described below.

GPC apparatus: HLC-8220GPC (manufactured by Tosoh Corporation)
Column: 5 columns consisting of TSKgel guardcolumn SuperMP(HZ)-N(1 column) and TSKgel SuperMultiporeHZ-N(4 columns) were connected in series and used.
Detector: RI
Sample concentration: 5 mg/ml (tetrahydrofuran solution)
Column temperature: 40° C.
Standard sample: Polystyrene <Gel Formation Evaluation (I)>

The aqueous gelling agent compositions 1 to 16 shown in Table 3, commercially available viscosity modifiers shown below (Comparative Examples 4 to 6), and another urethane polymer-type aqueous gelling agent composition (Comparative Example 7) were blended in blending amounts shown in Table 4 (0.5 part by mass to 10 parts by mass) into water or butylene glycol (BG) to produce aqueous gels 1 to 20. A case in which gelation was achieved was represented as "Gelation" and a case in which gelation was not achieved was represented as "No gelation." A blending amount shown in Table 4 is the blending amount of a gelling agent (active components excluding water and butylene glycol) with respect to 100 parts by mass of the total amount of water and butylene glycol, and the aqueous gelling agent composition 16 used water and butylene glycol at a mass ratio of water to butylene glycol of 2:5.

Comparative Example 4: Hydroxymethylcellulose (product name: HEC, manufactured by Sumitomo Seika Chemicals Company, Ltd.)

TABLE 3

| | | Type of compound (A) | Type of compound (B) | Mass ratio of compound (A) | Mass ratio of compound (B) | Water content (%) | BG content (%) |
|---|---|---|---|---|---|---|---|
| Comparative Example 1 | Aqueous gelling agent composition 1 | Compound (A)-1 | — | 100 | 0 | 70 | 0 |
| Comparative Example 2 | Aqueous gelling agent composition 2 | Compound (A)-1 | Compound (B)-1 | 98 | 2 | 70 | 0 |
| Example 1 | Aqueous gelling agent composition 3 | Compound (A)-1 | Compound (B)-1 | 95 | 5 | 70 | 0 |
| Example 2 | Aqueous gelling agent composition 4 | Compound (A)-1 | Compound (B)-1 | 93 | 7 | 70 | 0 |
| Example 3 | Aqueous gelling agent composition 5 | Compound (A)-1 | Compound (B)-1 | 90 | 10 | 70 | 0 |
| Example 4 | Aqueous gelling agent composition 6 | Compound (A)-1 | Compound (B)-1 | 85 | 15 | 70 | 0 |
| Comparative Example 3 | Aqueous gelling agent composition 7 | Compound (A)-1 | Compound (B)-1 | 80 | 20 | 70 | 0 |
| Example 5 | Aqueous gelling agent composition 8 | Compound (A)-2 | Compound (B)-2 | 90 | 10 | 70 | 0 |
| Example 6 | Aqueous gelling agent composition 9 | Compound (A)-3 | Compound (B)-3 | 90 | 10 | 70 | 0 |
| Example 7 | Aqueous gelling agent composition 10 | Compound (A)-4 | Compound (B)-4 | 90 | 10 | 70 | 0 |
| Example 8 | Aqueous gelling agent composition 11 | Compound (A)-5 | Compound (B)-5 | 90 | 10 | 70 | 0 |
| Example 9 | Aqueous gelling agent composition 12 | Compound (A)-6 | Compound (B)-6 | 90 | 10 | 70 | 0 |
| Example 10 | Aqueous gelling agent composition 13 | Compound (A)-7 | Compound (B)-1 | 90 | 10 | 70 | 0 |
| Example 11 | Aqueous gelling agent composition 14 | Compound (A)-8 | Compound (B)-7 | 90 | 10 | 70 | 0 |
| Example 12 | Aqueous gelling agent composition 15 | Compound (A)-9 | Compound (B)-8 | 90 | 10 | 70 | 0 |
| Example 13 | Aqueous gelling agent composition 16 | Compound (A)-1 | Compound (B)-1 | 90 | 10 | 20 | 50 |

Comparative Example 5: Methylcellulose (product name: Mecellose MC, manufactured by Tomoe Engineering Co., Ltd.)

Comparative Example 6: Carboxyvinyl polymer (product name: Carbopol 980, manufactured by The Lubrizol Corporation)

Comparative Example 7: The other urethane polymer-type aqueous gelling agent composition containing compound (A) represented by the following general formula (8) and compound (B) represented by the following general formula (9) at a mass ratio (A):(B) of 90:10

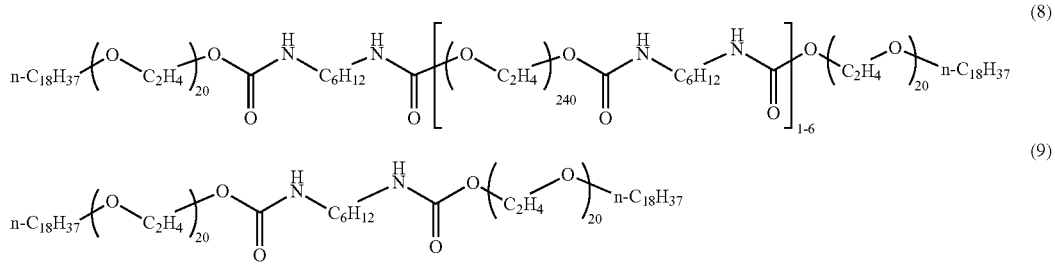

TABLE 4

|  | Gelling agent | Aqueous gel | Blending amount (0.5 part by mass) | Blending amount (1 part by mass) | Blending amount (3 parts by mass) | Blending amount (5 parts by mass) | Blending amount (10 parts by mass) |
| --- | --- | --- | --- | --- | --- | --- | --- |
| Comparative Example 8 | Aqueous gelling agent composition 1 | Aqueous gel 1 |  | No gelation |  |  | Gelation |
| Comparative Example 9 | Aqueous gelling agent composition 2 | Aqueous gel 2 |  | No gelation |  |  | Gelation |
| Example 14 | Aqueous gelling agent composition 3 | Aqueous gel 3 |  |  | Gelation |  |  |
| Example 15 | Aqueous gelling agent composition 4 | Aqueous gel 4 |  |  | Gelation |  |  |
| Example 16 | Aqueous gelling agent composition 5 | Aqueous gel 5 |  |  | Gelation |  |  |
| Example 17 | Aqueous gelling agent composition 6 | Aqueous gel 6 |  |  | Gelation |  |  |
| Comparative Example 10 | Aqueous gelling agent composition 7 | Aqueous gel 7 |  | No gelation |  |  | Gelation |
| Example 18 | Aqueous gelling agent composition 8 | Aqueous gel 8 |  |  | Gelation |  |  |
| Example 19 | Aqueous gelling agent composition 9 | Aqueous gel 9 |  |  | Gelation |  |  |
| Example 20 | Aqueous gelling agent composition 10 | Aqueous gel 10 |  |  | Gelation |  |  |
| Example 21 | Aqueous gelling agent composition 11 | Aqueous gel 11 |  |  | Gelation |  |  |
| Example 22 | Aqueous gelling agent composition 12 | Aqueous gel 12 |  |  | Gelation |  |  |
| Example 23 | Aqueous gelling agent composition 13 | Aqueous gel 13 |  |  | Gelation |  |  |
| Example 24 | Aqueous gelling agent composition 14 | Aqueous gel 14 |  |  | Gelation |  |  |
| Example 25 | Aqueous gelling agent composition 15 | Aqueous gel 15 |  |  | Gelation |  |  |
| Example 26 | Aqueous gelling agent composition 16 | Aqueous gel 16 |  |  | Gelation |  |  |
| Comparative Example 11 | Hydroxymethylcellulose | Aqueous gel 17 | No gelation |  |  | Gelation |  |
| Comparative Example 12 | Methylcellulose | Aqueous gel 18 | No gelation |  |  | Gelation |  |
| Comparative Example 13 | Carboxyvinyl polymer | Aqueous gel 19 |  |  | Gelation |  |  |
| Comparative Example 14 | Other urethane polymer-type aqueous gelling agent composition | Aqueous gel 20 |  | No gelation |  |  | Gelation |

<Gel Behavior Evaluation (I)>

The aqueous gels 1 to 20 shown in Table 4 were subjected to behavior evaluation. Evaluation items are the elasticity of gel (bouncy feel) and the softness of gel (ease of spread on the skin), and a test method and evaluation methods are as described below.

(Test Method)

First, each aqueous gel obtained in Table 4 was taken in a hand, and whether or not the gel had elasticity (bouncy feel) was evaluated. Next, the gel was spread on the back of the hand, and the softness of the gel (ease of spread on the skin) was evaluated.

(Evaluation Method: Evaluation for Elasticity)

Elasticity is present: The gel has elasticity (bouncy feel)

Elasticity is absent: The gel does not have elasticity (bouncy feel).

(Evaluation Method: Evaluation for Softness)

Evaluation a: The gel has satisfactory softness, and is also satisfactory in terms of spread on the skin.

Evaluation b: The gel has softness, but cannot be said to be satisfactory in terms of spread on the skin.

Evaluation c: The gel does not have softness.

The evaluation results are shown in Table 5. The samples that caused no gelation in Table 4 were not evaluated.

<Self-leveling Property Test (I)>

The aqueous gels 1 to 20 obtained in Table 4 were each evaluated for a self-leveling property. A test method is as described below.

(Test Method)

First, each aqueous gel obtained in Table 4 was placed in a circular container having a diameter of 5 centimeters and a depth of 3 centimeters, and was stirred with a spatula in three large clockwise rotations to apply a stimulus to the aqueous gel. After that, the length of time it took for the surface of the aqueous gel to return to a leveled state was measured, and an evaluation was made.

(Evaluation Method)

Evaluation A: The surface of the gel returned to a leveled state within 10 seconds after the application of the stimulus to the gel.

Evaluation B: The surface of the gel returned to a leveled state within 30 seconds after the application of the stimulus to the gel.

Evaluation C: The surface of the gel returned to a leveled state within 60 seconds after the application of the stimulus to the gel.

Evaluation D: The surface of the gel returned to a leveled state within 1 hour after the application of the stimulus to the gel.

TABLE 5

| | Gelling agent | Aqueous gel | Blending amount (0.5 part by mass) | Blending amount (1 part by mass) | Blending amount (3 parts by mass) | Blending amount (5 parts by mass) | Blending amount (10 parts by mass) |
|---|---|---|---|---|---|---|---|
| Comparative Example 8 | Aqueous gelling agent composition 1 | Aqueous gel 1 | | | | | Absent c |
| Comparative Example 9 | Aqueous gelling agent composition 2 | Aqueous gel 2 | | | | | Absent c |
| Example 14 | Aqueous gelling agent composition 3 | Aqueous gel 3 | Present a | Present a | Present a | Present b | Present c |
| Example 15 | Aqueous gelling agent composition 4 | Aqueous gel 4 | Present a | Present a | Present a | Present b | Present c |
| Example 16 | Aqueous gelling agent composition 5 | Aqueous gel 5 | Present a | Present a | Present a | Present b | Present c |
| Example 17 | Aqueous gelling agent composition 6 | Aqueous gel 6 | Present a | Present a | Present a | Present b | Present c |
| Comparative Example 10 | Aqueous gelling agent composition 7 | Aqueous gel 7 | | | | | Absent c |
| Example 18 | Aqueous gelling agent composition 8 | Aqueous gel 8 | Present a | Present a | Present a | Present b | Present c |
| Example 19 | Aqueous gelling agent composition 9 | Aqueous gel 9 | Present a | Present a | Present a | Present b | Present c |
| Example 20 | Aqueous gelling agent composition 10 | Aqueous gel 10 | Present a | Present a | Present a | Present b | Present c |
| Example 21 | Aqueous gelling agent composition 11 | Aqueous gel 11 | Present a | Present a | Present a | Present b | Present c |
| Example 22 | Aqueous gelling agent composition 12 | Aqueous gel 12 | Present a | Present a | Present a | Present b | Present c |
| Example 23 | Aqueous gelling agent composition 13 | Aqueous gel 13 | Present a | Present a | Present a | Present b | Present c |
| Example 24 | Aqueous gelling agent composition 14 | Aqueous gel 14 | Present a | Present a | Present a | Present b | Present c |
| Example 25 | Aqueous gelling agent composition 15 | Aqueous gel 15 | Present a | Present a | Present a | Present b | Present c |
| Example 26 | Aqueous gelling agent composition 16 | Aqueous gel 16 | Present a | Present a | Present a | Present b | Present c |
| Comparative Example 11 | Hydroxymethylcellulose | Aqueous gel 17 | | Absent a | Absent b | Absent c | Absent c |
| Comparative Example 12 | Methylcellulose | Aqueous gel 18 | | Absent a | Absent b | Absent c | Absent c |
| Comparative Example 13 | Carboxyvinyl polymer | Aqueous gel 19 | Absent b | Absent b | Absent c | Absent c | Absent c |
| Comparative Example 14 | Other urethane polymer-type aqueous gelling agent composition | Aqueous gel 20 | | | | | Absent c |

Evaluation E: The surface of the gel did not return to a leveled state even after more than 1 hour from the application of the stimulus to the gel.

The evaluation results are shown in Table 6. The samples that caused no gelation in Table 4 were not evaluated.

TABLE 6

| | Gelling agent | Aqueous gel | Blending amount (0.5 part by mass) | Blending amount (1 part by mass) | Blending amount (3 parts by mass) | Blending amount (5 parts by mass) | Blending amount (10 parts by mass) |
|---|---|---|---|---|---|---|---|
| Comparative Example 8 | Aqueous gelling agent composition 1 | Aqueous gel 1 | | | | | C |
| Comparative Example 9 | Aqueous gelling agent composition 2 | Aqueous gel 2 | | | | | C |
| Example 14 | Aqueous gelling agent composition 3 | Aqueous gel 3 | A | A | B | C | E |
| Example 15 | Aqueous gelling agent composition 4 | Aqueous gel 4 | A | A | B | C | E |
| Example 16 | Aqueous gelling agent composition 5 | Aqueous gel 5 | A | A | B | C | E |
| Example 17 | Aqueous gelling agent composition 6 | Aqueous gel 6 | A | A | B | C | E |
| Comparative Example 10 | Aqueous gelling agent composition 7 | Aqueous gel 7 | | | | | A |
| Example 18 | Aqueous gelling agent composition 8 | Aqueous gel 8 | A | A | A | B | C |
| Example 19 | Aqueous gelling agent composition 9 | Aqueous gel 9 | A | A | A | B | C |
| Example 20 | Aqueous gelling agent composition 10 | Aqueous gel 10 | A | A | B | C | E |
| Example 21 | Aqueous gelling agent composition 11 | Aqueous gel 11 | A | A | B | C | E |
| Example 22 | Aqueous gelling agent composition 12 | Aqueous gel 12 | A | A | B | C | E |
| Example 23 | Aqueous gelling agent composition 13 | Aqueous gel 13 | A | A | B | C | E |
| Example 24 | Aqueous gelling agent composition 14 | Aqueous gel 14 | A | A | B | C | E |
| Example 25 | Aqueous gelling agent composition 15 | Aqueous gel 15 | A | A | B | C | E |
| Example 26 | Aqueous gelling agent composition 16 | Aqueous gel 16 | A | A | B | C | E |
| Comparative Example 11 | Hydroxymethylcellulose | Aqueous gel 17 | | A | C | D | D |
| Comparative Example 12 | Methylcellulose | Aqueous gel 18 | | A | C | D | D |
| Comparative Example 13 | Carboxyvinyl polymer | Aqueous gel 19 | E | E | E | E | E |
| Comparative Example 14 | Other urethane polymer-type aqueous gelling agent composition | Aqueous gel 20 | | | | | D |

<Evaluation for Use with Spray Bottle (I)>

The aqueous gels 1 to 20 shown in Table 4 were each evaluated for usability with a spray bottle. A test method is as described below.

(Test Method)

First, each aqueous gel obtained in Table 4 was placed in a cylindrical spray bottle having a diameter of 2.5 centimeters and a depth of 6 centimeters. Then, a shearing stress was applied to the gel by a spraying operation, and whether the gel was able to be sprayed from the spray bottle was evaluated.

(Evaluation Method: Evaluation for Spray)

Evaluation 4: Easily sprayed from the spray bottle

Evaluation 3: Sprayed from the spray bottle

Evaluation 2: Not sprayed from the spray bottle, but jetted therefrom

Evaluation 1: Not jetted from the spray bottle

The evaluation results are shown in Table 7. The samples that caused no gelation in Table 4 were not evaluated.

TABLE 7

| | Gelling agent | Aqueous gel | Blending amount (0.5 part by mass) | Blending amount (1 part by mass) | Blending amount (3 parts by mass) | Blending amount (5 parts by mass) | Blending amount (10 parts by mass) |
|---|---|---|---|---|---|---|---|
| Comparative Example 8 | Aqueous gelling agent composition 1 | Aqueous gel 1 | | | | | 2 |

TABLE 7-continued

|  | Gelling agent | Aqueous gel | Blending amount (0.5 part by mass) | Blending amount (1 part by mass) | Blending amount (3 parts by mass) | Blending amount (5 parts by mass) | Blending amount (10 parts by mass) |
|---|---|---|---|---|---|---|---|
| Comparative Example 9 | Aqueous gelling agent composition 2 | Aqueous gel 2 |  |  |  |  | 2 |
| Example 14 | Aqueous gelling agent composition 3 | Aqueous gel 3 | 4 | 4 | 3 | 3 | 2 |
| Example 15 | Aqueous gelling agent composition 4 | Aqueous gel 4 | 4 | 4 | 3 | 3 | 2 |
| Example 16 | Aqueous gelling agent composition 5 | Aqueous gel 5 | 4 | 4 | 3 | 3 | 2 |
| Example 17 | Aqueous gelling agent composition 6 | Aqueous gel 6 | 4 | 4 | 3 | 3 | 2 |
| Comparative Example 10 | Aqueous gelling agent composition 7 | Aqueous gel 7 |  |  |  |  | 2 |
| Example 18 | Aqueous gelling agent composition 8 | Aqueous gel 8 | 4 | 4 | 3 | 3 | 2 |
| Example 19 | Aqueous gelling agent composition 9 | Aqueous gel 9 | 4 | 4 | 3 | 3 | 2 |
| Example 20 | Aqueous gelling agent composition 10 | Aqueous gel 10 | 4 | 4 | 3 | 3 | 2 |
| Example 21 | Aqueous gelling agent composition 11 | Aqueous gel 11 | 4 | 4 | 3 | 3 | 2 |
| Example 22 | Aqueous gelling agent composition 12 | Aqueous gel 12 | 4 | 4 | 3 | 3 | 2 |
| Example 23 | Aqueous gelling agent composition 13 | Aqueous gel 13 | 4 | 4 | 3 | 3 | 2 |
| Example 24 | Aqueous gelling agent composition 14 | Aqueous gel 14 | 4 | 4 | 3 | 3 | 2 |
| Example 25 | Aqueous gelling agent composition 15 | Aqueous gel 15 | 4 | 4 | 3 | 3 | 2 |
| Example 26 | Aqueous gelling agent composition 16 | Aqueous gel 16 | 4 | 4 | 3 | 3 | 2 |
| Comparative Example 11 | Hydroxymethylcellulose | Aqueous gel 17 |  | 1 | 1 | 1 | 1 |
| Comparative Example 12 | Methylcellulose | Aqueous gel 18 |  | 1 | 1 | 1 | 1 |
| Comparative Example 13 | Carboxyvinyl polymer | Aqueous gel 19 | 3 | 2 | 1 | 1 | 1 |
| Comparative Example 14 | Other urethane polymer-type aqueous gelling agent composition | Aqueous gel 20 |  |  |  |  | 2 |

The foregoing results revealed that each aqueous gel obtained using the aqueous gelling agent composition of the present invention was an elastic and soft gel, and was an aqueous gel having satisfactory self-leveling performance and a characteristic property of being usable with a spray bottle.

Next, the aqueous gelling agent compositions 4, 5, 10, 12, 13, and 14 (products of Examples) shown in Table 3 used in the gel formation evaluation (I) were each blended as a gelling agent into an emulsified composition, and the effect of the gelling agent in the blending of a cosmetic was confirmed.

<Gel Formation Evaluation (II)>

The blending of the emulsified composition into which the gelling agent is blended is shown in Table 8. The blending amount of each component (except water) in the emulsified composition shown in Table 8 represents a blending amount (parts by mass) with respect to 100 parts by mass of water.

TABLE 8

| Cosmetic label name | Blending amount (parts by mass) |
|---|---|
| Steareth-5 | 2.5 |
| Ceteth-25 | 2.5 |

TABLE 8-continued

| Cosmetic label name | Blending amount (parts by mass) |
|---|---|
| Cetyl ethylhexanoate | 6.25 |
| Mineral oil | 6.25 |
| BG | 6.25 |
| Water | 100 |

The aqueous gelling agent compositions 4, 5, 10, 12, 13, and 14 (products of Examples) shown in Table 3 were added in various blending amounts (0.5 part by mass to 5 parts by mass) to the emulsified composition shown in Table 8 in an attempt to produce gel-like emulsified compositions 1 to 6. The blending amount of the gelling agent shown in Table 9 is the blending amount of the aqueous gelling agent (active component) with respect to 100 parts by mass of the total amount of water and BG.

TABLE 9

| | Gelling agent | Emulsified composition | Blending amount (0.5 part by mass) | Blending amount (1 part by mass) | Blending amount (3 parts by mass) | Blending amount (5 parts by mass) |
|---|---|---|---|---|---|---|
| Example 27 | Aqueous gelling agent composition 4 | Emulsified composition 1 | | Gelation | | |
| Example 28 | Aqueous gelling agent composition 5 | Emulsified composition 2 | | Gelation | | |
| Example 29 | Aqueous gelling agent composition 10 | Emulsified composition 3 | | Gelation | | |
| Example 30 | Aqueous gelling agent composition 12 | Emulsified composition 4 | | Gelation | | |
| Example 31 | Aqueous gelling agent composition 13 | Emulsified composition 5 | | Gelation | | |
| Example 32 | Aqueous gelling agent composition 14 | Emulsified composition 6 | | Gelation | | |

<Gel Behavior Evaluation (II)>

The emulsified compositions 1 to 6 shown in Table 9 were subjected to behavior evaluation. Evaluation items are similar to those of the gel behavior evaluation (I), i.e., the elasticity of the emulsified composition (bouncy feel) and the softness of the emulsified composition (ease of spread on the skin), and a test method and evaluation methods are also similar to those of the gel behavior evaluation (I) as described below. The evaluation results are shown in Table 10.

(Test Method)

First, each emulsified composition obtained in Table 9 was taken in a hand, and whether or not the emulsified composition had elasticity (bouncy feel) was evaluated. Next, the emulsified composition was spread on the back of the hand, and the softness of the emulsified composition (ease of spread on the skin) was evaluated.

(Evaluation Method: Evaluation for Elasticity)

Elasticity is present: The emulsified composition has elasticity (bouncy feel).

Elasticity is absent: The emulsified composition does not have elasticity (bouncy feel).

(Evaluation Method: Evaluation for Softness)

Evaluation a: The emulsified composition has satisfactory softness, and is also satisfactory in terms of spread on the skin.

Evaluation b: The emulsified composition has softness, but cannot be said to be satisfactory in terms of spread on the skin.

Evaluation c: The emulsified composition does not have softness.

<Self-leveling Property Test (II)>

The emulsified compositions 1 to 6 obtained in Table 9 were each evaluated for a self-leveling property. A test method is as described below. The evaluation results are shown in Table 11.

(Test Method)

First, each emulsified composition obtained in Table 9 was placed in a circular container having a diameter of 5 centimeters and a depth of 3 centimeters, and was stirred with a spatula in three large clockwise rotations to apply a stimulus to the emulsified composition. After that, the length of time it took for the surface of the emulsified composition to return to a leveled state was measured, and an evaluation was made.

(Evaluation Method)

Evaluation A: The surface of the emulsified composition returned to a leveled state within 10 seconds after the application of the stimulus to the emulsified composition.

Evaluation B: The surface of the emulsified composition returned to a leveled state within 30 seconds after the application of the stimulus to the emulsified composition.

Evaluation C: The surface of the emulsified composition returned to a leveled state within 60 seconds after the application of the stimulus to the emulsified composition.

Evaluation D: The surface of the emulsified composition returned to a leveled state within 1 hour after the application of the stimulus to the emulsified composition.

Evaluation E: The surface of the emulsified composition did not return to a leveled state even after more than 1 hour from the application of the stimulus to the emulsified composition.

TABLE 10

| | Gelling agent | Emulsified composition | Blending amount (0.5 part by mass) | Blending amount (1 part by mass) | Blending amount (3 parts by mass) | Blending amount (5 parts by mass) |
|---|---|---|---|---|---|---|
| Example 27 | Aqueous gelling agent composition 4 | Emulsified composition 1 | Present a | Present a | Present b | Present b |
| Example 28 | Aqueous gelling agent composition 5 | Emulsified composition 2 | Present a | Present a | Present b | Present b |
| Example 29 | Aqueous gelling agent composition 10 | Emulsified composition 3 | Present a | Present a | Present b | Present b |
| Example 30 | Aqueous gelling agent composition 12 | Emulsified composition 4 | Present a | Present a | Present b | Present b |
| Example 31 | Aqueous gelling agent composition 13 | Emulsified composition 5 | Present a | Present a | Present b | Present b |
| Example 32 | Aqueous gelling agent composition 14 | Emulsified composition 6 | Present a | Present a | Present b | Present b |

TABLE 11

| | Gelling agent | Emulsified composition | Blending amount (0.5 part by mass) | Blending amount (1 part by mass) | Blending amount (3 parts by mass) | Blending amount (5 parts by mass) |
|---|---|---|---|---|---|---|
| Example 27 | Aqueous gelling agent composition 4 | Emulsified composition 1 | A | A | C | C |
| Example 28 | Aqueous gelling agent composition 5 | Emulsified composition 2 | A | A | C | C |
| Example 29 | Aqueous gelling agent composition 10 | Emulsified composition 3 | A | A | C | C |
| Example 30 | Aqueous gelling agent composition 12 | Emulsified composition 4 | A | A | C | C |
| Example 31 | Aqueous gelling agent composition 13 | Emulsified composition 5 | A | A | C | C |
| Example 32 | Aqueous gelling agent composition 14 | Emulsified composition 6 | A | A | C | C |

<Evaluation for Use with Spray Bottle (I)>

The emulsified compositions 1 to 6 shown in Table 9 were each evaluated for usability with a spray bottle. A test method is as described below. The evaluation results are shown in Table 12.

(Test Method)

First, each emulsified composition obtained in Table 9 was placed in a cylindrical spray bottle having a diameter of 2.5 centimeters and a depth of 6 centimeters. Then, a shearing stress was applied to the emulsified composition by a spraying operation, and whether the emulsified composition was able to be sprayed from the spray bottle was evaluated.

(Evaluation Method: Evaluation for Spray)
Evaluation 4: Easily sprayed from the spray bottle
Evaluation 3: Sprayed from the spray bottle
Evaluation 2: Not sprayed from the spray bottle, but jetted therefrom
Evaluation 1: Not jetted from the spray bottle

TABLE 12

| | Gelling agent | Emulsified composition | Blending amount (0.5 part by mass) | Blending amount (1 part by mass) | Blending amount (3 parts by mass) | Blending amount (5 parts by mass) |
|---|---|---|---|---|---|---|
| Example 27 | Aqueous gelling agent composition 4 | Emulsified composition 1 | 4 | 4 | 3 | 3 |
| Example 28 | Aqueous gelling agent composition 5 | Emulsified composition 2 | 4 | 4 | 3 | 3 |
| Example 29 | Aqueous gelling agent composition 10 | Emulsified composition 3 | 4 | 4 | 3 | 3 |
| Example 30 | Aqueous gelling agent composition 12 | Emulsified composition 4 | 4 | 4 | 3 | 3 |
| Example 31 | Aqueous gelling agent composition 13 | Emulsified composition 5 | 4 | 4 | 3 | 3 |
| Example 32 | Aqueous gelling agent composition 14 | Emulsified composition 6 | 4 | 4 | 3 | 3 |

The foregoing results revealed that each emulsified composition (cosmetic) having blended therein the aqueous gelling agent composition of the present invention was an elastic and soft gel-like emulsified composition, and was a gel-like emulsified composition having satisfactory self-leveling performance and a characteristic property of being usable with a spray bottle.

The present international application claims priority based on Japanese Patent Application No. 2016-168932 filed on Aug. 31, 2016, the contents of which are incorporated herein by reference in their entirety.

INDUSTRIAL APPLICABILITY

The aqueous gelling agent composition of the present invention is an additive that gives an aqueous gel having both characteristic elasticity and softness, i.e., having a self-leveling property and being usable with a spray bottle. The aqueous gel can be used in all kinds of applications, and particularly in the field of cosmetics, its usefulness is very high because a gel exhibiting behavior that has not been obtained with a hitherto known gelling agent is given.

The invention claimed is:

1. An aqueous gelling agent composition, comprising:
Compound (A) represented by the following formula (1); and Compound (B) represented by the following formula (2), wherein a mass ratio of compound (A) to compound (B), (A):(B), is from 95:5 to 85:15:

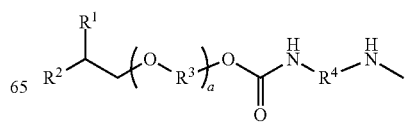

(1)

-continued

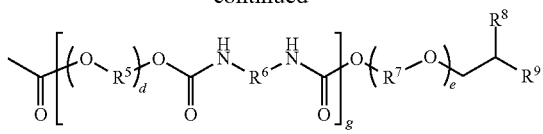

wherein $R^1$ is a decyl group, $R^2$ is a dodecyl group, $R^3$ is an ethylene group, $R^4$ is a hexyl group, $R^5$ is an ethylene group, $R^6$ is a hexyl group, $R^7$ is an ethylene group, $R^8$ is a decyl group, $R^9$ is a dodecyl group, a is 20, d is 240, e is 20, and g is a number of 1 to 10; and (2)

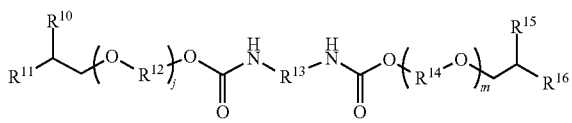

wherein $R^{10}$ is a decyl group, $R^{11}$ is a dodecyl group, $R^{12}$ is an ethylene group, $R^{13}$ is a hexyl group, $R^{14}$ is an ethylene group, $R^{15}$ is a decyl group, $R^{16}$ is a dodecyl group, j is 20, and m is 20.

2. An aqueous gel, comprising:
the aqueous gelling agent composition of claim 1;
a solvent; and
a polyol compound.

3. The aqueous gel according to claim 2, wherein an amount of the aqueous gelling agent composition is from 0.1 part by mass to 5 parts by mass with respect to 100 parts by mass of a total amount of the solvent and the polyol compound.

4. An aqueous cosmetic, comprising:
a solvent;
a polyol compound; and
0.1 part by mass to 5 parts by mass of the aqueous gelling agent composition of claim 1 with respect to 100 parts by mass of a total amount of the solvent and the polyol compound in the cosmetic.

5. A method of obtaining a gel-like aqueous cosmetic having a self-leveling property and being usable with a spray bottle, the method comprising adding the aqueous gelling agent composition of claim 1 to an aqueous cosmetic.

* * * * *